(12) United States Patent
Narasimhan et al.

(10) Patent No.: US 10,702,171 B2
(45) Date of Patent: Jul. 7, 2020

(54) SYSTEMS, DEVICES, AND METHODS FOR MEASURING BLOOD PRESSURE OF A USER

(71) Applicant: Apple Inc., Cupertino, CA (US)

(72) Inventors: Ravi Narasimhan, Sunnyvale, CA (US); Zijing Zeng, Cupertino, CA (US); Richard C. Kimoto, Cupertino, CA (US); Erno Klaassen, Cupertino, CA (US); Thomas J. Sullivan, Cupertino, CA (US); Derek Park-Shing Young, Cupertino, CA (US); Todd K. Whitehurst, Cupertino, CA (US)

( * ) Notice: Subject to any disclaimer, the term of this patent is extended or adjusted under 35 U.S.C. 154(b) by 59 days.

(21) Appl. No.: 15/507,659

(22) PCT Filed: Sep. 8, 2015

(86) PCT No.: PCT/US2015/048839
§ 371 (c)(1),
(2) Date: Feb. 28, 2017

(87) PCT Pub. No.: WO2016/040256
PCT Pub. Date: Mar. 17, 2016

(65) Prior Publication Data
US 2017/0360306 A1 Dec. 21, 2017

Related U.S. Application Data

(60) Provisional application No. 62/047,431, filed on Sep. 8, 2014.

(51) Int. Cl.
*A61B 5/022* (2006.01)
*A61B 5/00* (2006.01)
*A61B 5/021* (2006.01)

(52) U.S. Cl.
CPC ............ *A61B 5/022* (2013.01); *A61B 5/0053* (2013.01); *A61B 5/02108* (2013.01);
(Continued)

(58) Field of Classification Search
CPC ... A61B 5/022; A61B 5/0053; A61B 5/02108; A61B 5/02125; A61B 5/681;
(Continued)

(56) References Cited

U.S. PATENT DOCUMENTS 4,269,193 A * 5/1981 Eckerle .............. A61B 5/02116
600/485
6,176,831 B1 1/2001 Voss et al.
(Continued)

FOREIGN PATENT DOCUMENTS

| EP | 1602325 | 12/2005 |
|---|---|---|
| WO | 2015193551 | 12/2015 |
| WO | 2016040256 | 3/2016 |

OTHER PUBLICATIONS

"National, State, and Local Area Vaccination Coverage Among Children Aged 19-35 Months—United States, 2011", Morbidity Mortality Weekly Report Weekly, vol. 61 No. 35, Sep. 7, 2012, 24 pages.

(Continued)

*Primary Examiner* — Matthew Kremer
*Assistant Examiner* — Avery M Foley
(74) *Attorney, Agent, or Firm* — Kilpatrick Townsend & Stockton LLP

(57) ABSTRACT

The present invention generally relates to blood pressure monitoring. In some embodiments, methods and devices of measuring a mean arterial pressure are provided and/or monitoring blood pressure changes. A wrist-worn device may include a plurality of sensors backed by a plurality of actuators. Subsets of the plurality of sensors may be selec-
(Continued)

tively actuateable against a wrist of a user using one or more of the plurality of actuators. A preferred sensor and location may be identified based on pressure signals received from each of the sensors. In some embodiments, devices may use a fluid bladder coupled with piezoelectric film sensors. A fluid bladder pressure sensor may be used to calibrate the piezoelectric film signal to provide a static and dynamic pressure reading. In yet another embodiment, a mean arterial pressure may be calculated by processing a swept pressure signal obtained as a sensor is swept through different heights.

17 Claims, 15 Drawing Sheets

(52) U.S. Cl.
CPC .......... *A61B 5/02125* (2013.01); *A61B 5/681* (2013.01); *A61B 5/6824* (2013.01); *A61B 2560/0223* (2013.01); *A61B 2562/028* (2013.01); *A61B 2562/0247* (2013.01); *A61B 2562/046* (2013.01)

(58) Field of Classification Search
CPC .......... A61B 5/6824; A61B 2560/0223; A61B 2562/0247; A61B 2562/028; A61B 2562/046
See application file for complete search history.

(56) References Cited

U.S. PATENT DOCUMENTS

| | | |
|---|---|---|
| 6,228,034 B1 | 5/2001 | Voss et al. |
| 6,443,906 B1 | 9/2002 | Ting et al. |
| 6,514,211 B1 | 2/2003 | Baura |
| 6,554,774 B1 | 4/2003 | Miele |
| 6,676,600 B1 | 1/2004 | Conero et al. |
| 6,705,990 B1 | 3/2004 | Gallant et al. |
| 6,730,038 B2 | 5/2004 | Gallant et al. |
| 6,918,879 B2 | 7/2005 | Ting et al. |
| 6,932,772 B2 | 8/2005 | Kan |
| 6,974,419 B1 | 12/2005 | Voss et al. |
| 7,048,691 B2 | 5/2006 | Miele et al. |
| 7,144,372 B2 | 12/2006 | Ng et al. |
| 7,291,112 B2 | 11/2007 | Martin et al. |
| 7,317,409 B2 | 1/2008 | Conero |
| 7,318,807 B2 | 1/2008 | Ng |
| 7,361,147 B2 | 4/2008 | Ng |
| 7,503,896 B2 | 3/2009 | Miele et al. |
| 7,503,897 B2 | 3/2009 | Ng et al. |
| 7,867,170 B2 | 1/2011 | Gallant et al. |
| 7,871,381 B2 | 1/2011 | Ng et al. |
| 7,871,382 B2 | 1/2011 | Ng |
| 7,946,994 B2 | 5/2011 | Finburgh et al. |
| 7,976,471 B2 | 7/2011 | Martin et al. |
| 8,157,730 B2 | 4/2012 | Leboeuf et al. |
| 8,204,786 B2 | 6/2012 | Leboeuf et al. |
| D666,169 S | 8/2012 | Tucker et al. |
| 8,251,903 B2 | 8/2012 | Leboeuf et al. |
| 8,323,982 B2 | 12/2012 | LeBoeuf et al. |
| 8,328,727 B2 | 12/2012 | Miele et al. |
| 8,469,895 B2 | 6/2013 | Ting et al. |
| 8,506,497 B2 | 8/2013 | Katayama et al. |
| 8,512,242 B2 | 8/2013 | Leboeuf et al. |
| 8,597,195 B2 | 12/2013 | Gallant et al. |
| 8,647,270 B2 | 2/2014 | Leboeuf et al. |
| 8,652,040 B2 | 2/2014 | Leboeuf et al. |
| 8,652,409 B2 | 2/2014 | LeBoeuf et al. |
| 8,657,753 B2 | 2/2014 | Ting et al. |
| 8,672,854 B2 | 3/2014 | Mccombie et al. |
| 8,700,111 B2 | 4/2014 | Leboeuf et al. |
| 8,702,607 B2 | 4/2014 | Leboeuf et al. |
| 8,777,862 B2 * | 7/2014 | Finburgh .............. A61B 5/022 600/481 |
| 8,788,002 B2 | 7/2014 | LeBoeuf et al. |
| 2002/0026121 A1 | 2/2002 | Kan et al. |
| 2003/0212335 A1 * | 11/2003 | Huang ................. A61B 5/021 600/500 |
| 2004/0059234 A1 * | 3/2004 | Martin .................. A61B 5/022 600/500 |
| 2008/0146890 A1 | 6/2008 | LeBoeuf et al. |
| 2008/0146892 A1 | 6/2008 | Leboeuf et al. |
| 2008/0220535 A1 | 9/2008 | LeBoeuf et al. |
| 2008/0294019 A1 * | 11/2008 | Tran ..................... A61B 5/0006 600/301 |
| 2009/0112071 A1 | 4/2009 | LeBoeuf et al. |
| 2010/0036209 A1 * | 2/2010 | Ferren ................. A61B 5/0002 600/301 |
| 2010/0286538 A1 | 11/2010 | Kim et al. |
| 2011/0213254 A1 | 9/2011 | Ting |
| 2013/0059396 A1 | 3/2013 | LeBoeuf et al. |
| 2013/0131519 A1 | 5/2013 | LeBoeuf et al. |
| 2013/0304112 A1 | 11/2013 | Ting et al. |
| 2014/0114147 A1 | 4/2014 | Romesburg |
| 2014/0128690 A1 | 5/2014 | LeBoeuf |
| 2014/0135596 A1 | 5/2014 | LeBoeuf et al. |
| 2014/0140567 A1 | 5/2014 | LeBoeuf et al. |
| 2014/0163399 A1 | 6/2014 | Gallant et al. |
| 2014/0171755 A1 | 6/2014 | LeBoeuf et al. |
| 2014/0171762 A1 | 6/2014 | LeBoeuf et al. |
| 2014/0180039 A1 | 6/2014 | LeBoeuf et al. |
| 2015/0112606 A1 | 4/2015 | He et al. |
| 2015/0164351 A1 | 6/2015 | He et al. |

OTHER PUBLICATIONS

"Non-invasive haemodynamic monitor", BioZ® Cardio Profile, 42 pages.

"Prevention, Detection, Evaluation, and Treatment of High Blood Pressure", National High Blood Pressure Education Program, The Seventh Report of the Joint National Committee, 2004, 104 pages.

"Pulse Transit Time and Velocity Calculation", Biopac Systems, Inc., Mar. 21, 2006, 3 pages.

Allen, "Photoplethysmography and its application in clinical physiological measurement", Physiol. Meas. vol. 28, 2007, pp. R1-R39.

Ashraf et al., "Size of radial and ulnar artery in local population", J Pak Med Assoc, vol. 60, No. 10, Oct. 2010, pp. 817-819.

Baheti et al., "An ultra low power pulse oximeter sensor based on compressed sensing", Body Sensor Networks, IEEE, 2009, pp. 144-148.

Cattivelli et al., "Noninvasive Cuffless Estimation of Blood Pressure from Pulse Arrival Time and Heart Rate with Adaptive Calibration", IEEE Computer Society, 2009, pp. 114-119.

Couceiro et al., "Characterization of Surrogate Parameters for Blood Pressure Regulation in Neurally-Mediated Syncope", 2013 35th Annual International Conference of the IEEE Engineering in Medicine and Biology Society (EMBC), 2013, pp. 5381-5385.

Critchley, "Minimally Invasive Cardiac Output Monitoring in the Year 2012", Artery Bypass, Mar. 13, 2013, pp. 45-80.

Cybulski et al., "Impedance Cardiography", Lecture Notes in Electrical Engineering, 2011, pp. 7-37.

Czajkowski et al., "Long-term Plan for Research and Translation in Hypertension for Enhancing Public Health", National Heart, Lung, and Blood Institute, National Institutes of Health Department of Health and Human Services, Dec. 2004, 77 pages.

Da Silva, "A pervasive system for real-time blood pressure Monitoring", Feb. 13, 2013, pp. 1-23.

Douniama, "Blood Pressure Estimation based on Pulse Transit Time and Compensation of Vertical Position", 3rd Russian-Bavarian Conference on Bio-Medical Engineering, 2007, 5 pages.

Douniama et al., "Blood Pressure Tracking Capabilities of Pulse Transit Times in Different Arterial Segments: A Clinical Evaluation", Computers in Cardiology, vol. 36, 2009, pp. 201-204.

Fagard, "Exercise characteristics and the blood pressure response to dynamic physical training", Med. Sci. Sports Exerc., vol. 33, No. 6,, 2001, pp. S484-S492.

(56) References Cited

OTHER PUBLICATIONS

Forouzanfar et al., "Coefficient-Free Blood Pressure Estimation Based on Pulse Transit Time—Cuff Pressure Dependence", IEEE Transactions on Biomedical Engineering, vol. 60, No. 7, Jul. 2013, pp. 1814-1824.
Gesche et al., "Continuous blood pressure measurement by using the pulse transit time: comparison to a cuff-based method", Eur J Appl Physiol, May 10, 2011, 7 pages.
Gesche et al., "Continuous blood pressure measurement by using the pulse transit time: comparison to a cuff-based method", Eur J Appl Physiol, vol. 112, 2012, pp. 309-315.
Harrison et al., "Portable acoustic myography—a realistic noninvasive method for assessment of muscle activity and coordination in human subjects in most home and sports settings", Physiological Reports ISSN 2051-817X, vol. 1, Iss.2, e00029, 2013, pp. 1-9.
Harwood-Smith et al., "Assessment of pulse transit time to indicate cardiovascular changes during obstetric spinal anaesthesia", British Journal of Anaesthesia, vol. 96 (1), 2006, pp. 100-105.
Hassan et al., "Non-invasive Continuous Blood Pressure Monitoring Based on PWTT", Journal of Advanced Computer Science and Technology Research, vol. 1, 2011, pp. 63-73.
He et al., "Evaluation of the Correlation Between Blood Pressure and Pulse Transit Time", IEEE, 2013, 4 pages.
Hennig et al., "Continuous blood pressure measurement using pulse transit time", Somnologie vol. 17, Jun. 6, 2013, pp. 104-110.
Hsiu et al., "Correlation of Harmonic Components between the Blood Pressure and Photoplethysmography Waveforms Following Local-Heating Stimulation", International Journal of Bioscience, Biochemistry and Bioinformatics, vol. 2, No. 4, Jul. 2012, pp. 248-253.
Hsiu et al., "Effects of Local-Heating Stimulation on the Harmonic Structure of the Blood Pressure and Photoplethysmography Waveforms", 2nd International Conference on Biomedical Engineering and Technology IPCBEE vol. 34, 2012, pp. 1-5.
Huotari et al., "Photoplethysmography and its detailed pulse waveform analysis for arterial stiffness", Rakenteiden Mekaniikka (Journal of Structural Mechanics), vol. 44, No. 4, 2011, pp. 345-362.
Jeong et al., "Continuous Blood Pressure Monitoring using Pulse Wave Transit Time", ICCAS, 2005, 4 pages.
Jobbagy, "Blood Pressure Measurement: Assessment of a Variable Quantity", 2010, pp. 316-324.
Kado et al., "RedTacton Near-body Electric-field Communications Technology and Its Applications", NTT Technical Review, vol. 8 No. 3, 2010, pp. 1-6.
Kalsi, "Design of Arterial Blood Pressure, Heart Rate Variability, and Breathing Rate Monitoring Device", Electrical and Biomedical Engineering Design Project (4BI6), Apr. 23, 2009, 65 pages.
Kim, "Design of Infrared Sensor Based Measurement System for Continuous Blood Pressure Monitoring Device", pp. 1-12.
Kim et al., "Development of an Arterial Tonometer Sensor", 31st Annual International Conference of the IEEE EMBS, Sep. 2-6, 2009, pp. 3771-3774.
Lima et al., "Use of Peripheral Perfusion Index Derived From the Pulse Oximetry Signal as a Noninvasive Indicator of Perfusion", Crit Care Med., vol. 30(6), 2002, 10 pages.
Marcinkevics et al., "Relationship between arterial pressure and pulse wave velocity using photoplethysmography during the post-exercise recovery period", Acta Universitatis Latviensis, vol. 753, Biology,, 2009, pp. 59-68.
Marinkovic, "Reconstructing the Blood Pressure Waveform using a Wearable Photoplethysmograph Sensor and Hydrostatic Pressure Variations Measured by Accelerometers", Submitted to the Department of Mechanical Engineering in Partial Fulfillment of the Requirements for the Degrees of Master of Science in Mechanical Engineering at the Massachusetts Institute of Technology, Feb. 2007, 54 pages.
Matthys et al., "Long-term pressure monitoring with arterial applanation tonometry: a non-invasive alternative during clinical intervention?", Technol Health Care, vol. 16, 2008, pp. 183-193.

McCarthy et al., "An examination of calibration intervals required for accurately tracking blood pressure using pulse transit time algorithms", Journal of Human Hypertension, 2013, pp. 1-7.
McCarthy, "An Investigation of Pulse Transit Time as a Non-Invasive Blood Pressure Measurement Method", Journal ofPhysics:ConferenceSeries. vol. 307, 2011, 6 pages.
McCombie et al., "Adaptive hydrostatic blood pressure calibration: Development of a wearable, autonomous pulse wave velocity blood pressure monitor", Proceedings of the 29th Annual International Conference of the IEEE EMBS, Aug. 23-26, 2007, pp. 370-373.
Meigas et al., "Continuous Blood Pressure Monitoring Using Pulse Wave Delay", 2001, 5 pages.
Nakamura et al., "Collaborative Processing of Wearable and Ambient Sensor System for Blood Pressure Monitoring", Sensors, 11, ISSN 1424-8220 www.mdpi.com/journal/sensors, 2011, pp. 6760-6770.
Norris et al., "AgeChangesinHeartRateandBloodPressure ResponsestoTiltingandStandardized Exercise", Circulation, vol. VIII, Downloaded from http://circ.ahajournals.org/ at Cons California Dig Lib, Aug. 26, 2013, pp. 521-526.
O'Brien, "European Society of Hypertension International Protocol revision 2010 for the validation of blood pressure measuring devices in adults", Blood Pressure Monitoring, vol. 15, 2010, pp. 23-28.
O'Brien et al., "Working Group on Blood Pressure Monitoring of the European Society of Hypertension International Protocol for validation of blood pressure measuring devices in adults", Blood Pressure Monitoring, vol. 7, 2002, pp. 3-17.
O'Brien, "The British Hypertension Society protocol for the evaluation of automated and semiautomated blood pressure measuring devices with special reference to ambulatory systems", Journal of Ambulatory Monitoring, vol. 4, No. 3,, 1991, pp. 207-228.
Payne et al., "Pulse transit time measured from the ECG: an unreliable marker of beat-to-beat blood pressure", J Appl Physiol vol. 100, Sep. 1, 2005, pp. 136-141.
Proenca et al., "Is Pulse Transit Time a good indicator of Blood Pressure changes during short physical exercise in a young population?", 32nd Annual International Conference of the IEEE EMBS, Aug. 31-Sep. 4, 20, pp. 598-601.
Raissuni et al., "Can We Obtain a Noninvasive and Continuous Estimation of Cardiac Output? Comparison Between Three Noninvasive Methods", Int Heart J, Nov. 2013, pp. 395-400.
Reisner et al., "Utility of the Photoplethysmogram in Circulatory Monitoring", Anesthesiology, vol. 108, 2008, pp. 950-958.
Sackl-Pietsch et al., "Continuous non-invasive arterial pressure shows high accuracy in comparison to invasive intra-arterial blood pressure measurement", pp. 1-5.
Seo, "Evaluation of cardiac output using nonuniform hybrid electrical impedance model based on forward lumped parameter and both-hands impedance measurement system", The Graduate School Yonsei University, Department of Biomedical Engineering, Feb. 2012, 146 pages.
Shaltis et al., "A Finite Element Analysis of Local Oscillometric Blood Pressure Measurements", Proceedings of the 29th Annual International Conference of the IEEE EMBS, Aug. 23-26, 2007, pp. 355-358.
Shaltis et al., "A hydrostatic pressure approach to cuffless blood pressure monitoring", Proceedings of the 26th Annual International Conference of the IEEE EMBS, Sep. 1-5, 2004, pp. 2173-2176.
Shaltis et al., "Calibration of the Photoplethysmogram to Arterial Blood Pressure: Capabilities and Limitations for Continuous Pressure Monitoring", Proceedings of the 2005 IEEE Engineering in Medicine and Biology 27th Annual Conference, Sep. 1-4, 2005, pp. 3970-3973.
Shaltis et al., "Cuffless Blood Pressure Monitoring Using Hydrostatic Pressure Changes", IEEE Transactions on Biomedical Engineering, vol. 55, No. 6,, Jun. 2008, pp. 1775-1777.
Shaltis et al., "Monitoring of Venous Oxygen Saturation Using a Novel Vibratory Oximetry Sensor", 2d Joint Conference of the IEEE Engineering in Medicine and Biology, Society and the Biomedical Engineering Society, Oct. 23-26, 2002, pp. 1722-1723.

(56) References Cited

OTHER PUBLICATIONS

Shaltis et al., "Wearable, Cuff-less PPG-Based Blood Pressure Monitor with Novel Height Sensor", Proceedings of the 28th IEEE EMBS Annual International Conference, Aug. 30-Sep. 3, 2006, pp. 908-911.
Silverberg, "The unsupported arm: a cause of falsely raised blood pressure readings", British Medical Journal, Nov. 19, 1977, p. 1331.
Sinha et al., "Non-Invasive Blood Pressure Monitor: Beat to Beat", Technology Development Article, BARC Newsletter, Issue No. 328, Sep.-Oct. 2012, pp. 62-68.
Smith et al., "Pulse transit time: an appraisal of potential clinical applications", Thorax vol. 54, Available online at: http://thorax.bmj.com/content/54/5/452.full.html, Oct. 13, 2013, pp. 452-458.
Sola et al., "Continuous non-invasive blood pressure estimation", Diss. ETH. No. 20093, 2011, 196 pages.
Sola et al., "Noninvasive and Nonocclusive Blood Pressure Estimation Via a Chest Sensor", IEEE Transactions on Biomedical Engineering, Vol. 60, No. 12, Dec. 2013, pp. 3505-3513.
Sola et al., "Non-invasive monitoring of central blood pressure by electrical impedance tomography: first experimental evidence", Med Biol Eng Comput, vol. 49, 2011, pp. 409-415.
Somnomedics, "Non-invasive, continuous and non-reactive blood pressure measurement using PTT", Medical Devices for Sleep Diagnostics and Therapy, 2012, pp. 1-20.
Song et al., "Estimation of Blood Pressure Using Photoplethysmography on the Wrist", Computers in Cardiology, vol. 36, 2009, pp. 741-744.
Sorvoja et al., "Noninvasive Blood Pressure Measurement Methods", Molecular and Quantum Acoustics, vol. 27, 2006, pp. 239-264.
Spulak et al., "Experiments With Blood Pressure Monitoring Using ECG and PPG", Czech Technical University in Prague, 5 pages.
Spulak et al., "Parameters for Mean Blood Pressure Estimation Based on Electrocardiography and Photoplethysmography", Czech Technical University in Prague, 4 pages.
Teja, "Calculation of Blood Pulse Transit Time from PPG", Department of Biotechnology and Medical Engineering National Institute of Technology, Rourkela 2012, 2012, 54 pages.
Theodor et al., "Implantable Acceleration Plethysmography for Blood Pressure Determination", 35th Annual International Conference of the IEEE EMBS, Jul. 3-7, 2013, pp. 4038-4041.
Thompson et al., "Arteriosclerosis, Thrombosis, and Vascular Biology", Arterioscler Thromb Vase Biol. vol. 23, American Heart Association, Available online at: http://atvb.ahajournals.org/, 2003, pp. e42-e49.
Townsend, "Oscillometry", Medical Electronics, Michaelmas Term, 2001, pp. 48-54.
Van Dijk et al., "Oscillometry and applanation tonometry measurements in older individuals with elevated levels of arterial stiffness", Analytical methods and statistical analysis, Blood Pressure Monitoring vol. 18 No. 6, 2013, pp. 332-338.
Vignon-Clementel et al., "A Coupled Multidomain Method for Computational Modeling of Blood Flow", A Dissertation Submitted to the Department of Mechanical Engineering and the Committee on Graduate Studies of Stanford University in Partial Fulfillment of the Requirements for the Degree of Doctor of Philosophy, Jun. 2006, 207 pages.
Ward, "Blood Pressure Measurement", Cont Edu Anaesth Crit Care & Pain.vol. 7(4), 2007, pp. 122-126.
Wibmer et al., "Pulse transit time and blood pressure during cardiopulmonary exercise tests", Physiological Research Pre-Press Article, 2014, 26 pages.
Wikipedia, "Continuous noninvasive arterial pressure", Available online at: http://en.wikipedia.org/wiki/Continuous_noninvasive_arterial_pressure, Jul. 24, 2013, 8 pages.
Woidtke, "Pulse Transit Time and Peripheral Arterial Tonometry", 33 pages.
Wong et al., "An Evaluation of the Cuffless Blood Pressure Estimation Based on Pulse Transit Time Technique: a Half Year Study on Normotensive Subjects", Cardiovasc Eng. vol. 9, 2009, pp. 32-38.
Wong et al., "The Relationship between Pulse Transit Time and Systolic Blood Pressure on Individual Subjects after Exercises", Proceedings of the 1st Distributed Diagnosis and Home Healthcare (D2H2) Conference, Apr. 2-4, 2006, pp. 37-38.
Ye et al., "Estimation of Systolic and Diastolic Pressure using the Pulse Transit Time", World Academy of Science, Engineering and Technology 43 2010 726, 2010, pp. 726-731.
Yong, "A computational system to optimise noise rejection in photoplethysmography signals during motion or poor perfusion states", Med Biol Eng Comput vol. 44, 2006, pp. 140-145.
Yoon et al., "Non-constrained Blood Pressure Monitoring Using ECG and PPG for Personal Healthcare", J Med Syst. vol. 33, 2009, pp. 261-266.
Zhang, "Cuff-Free Blood Pressure Estimation Using Signal Processing Techniques", Thesis for the degree of Master of Science in the Division of Biomedical Engineering University of Saskatchewan http://hdl.handle.net/10388/etd-09082010-164956, Aug. 2010, 73 pages.
Zhang et al., "Pulse arrival time is not an adequate surrogate for pulse transit time as a marker of blood pressure", J Appl Physiol vol. 111, 2011, pp. 1681-1686.

* cited by examiner

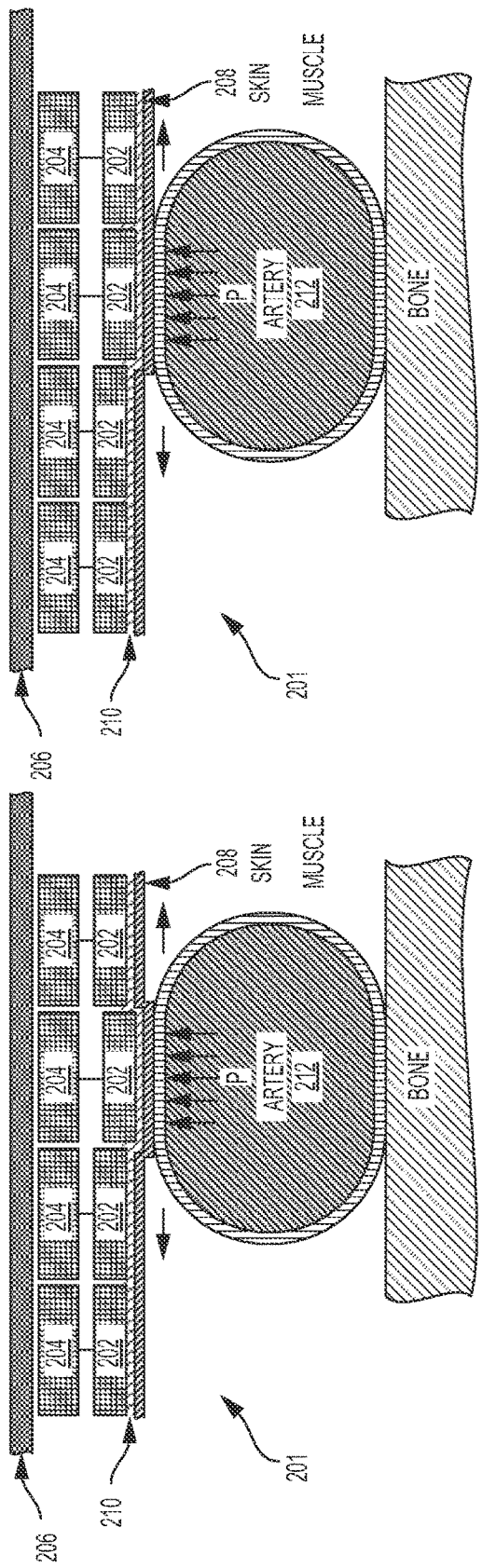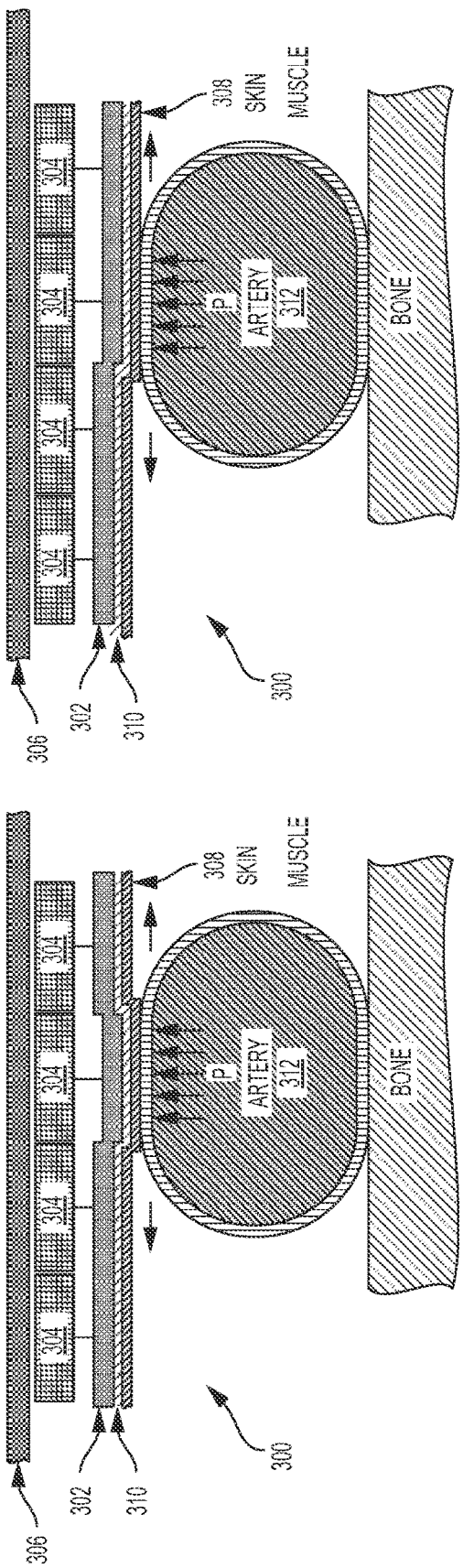
Fig. 16
Fig. 17
Fig. 18
Fig. 19

SYSTEMS, DEVICES, AND METHODS FOR MEASURING BLOOD PRESSURE OF A USER

CROSS-REFERENCES TO RELATED APPLICATIONS

The present application is a U.S. National Stage application of PCT/US2015/048839 filed Sep. 8, 2015; which claims the benefit of U.S. Provisional Appln. No. 62/047,431 filed Sep. 8, 2014, the full disclosures of which are incorporated herein by reference in their entirety for all purposes.

BACKGROUND OF THE INVENTION

The present invention generally relates to the measuring and monitoring of blood pressure. More specifically, embodiments may apply the theory of applanation tonometry for the measurement of blood pressure. Some embodiments provide a method for measuring mean arterial pressure. Some embodiments provide a device that may be worn by a user that may non-invasively measure and monitor absolute arterial pressure of a user.

Elevated blood pressure (a.k.a. hypertension) is a major risk factor for cardiovascular disease. As a result, blood pressure measurement is a routine task in many medical examinations. Timely detection of hypertension can help inhibit related cardiovascular damage via accomplishment of effective efforts in treating and/or controlling the subject's hypertension.

A person's blood pressure is a continuously changing vital parameter. As a result, sporadic office blood pressure measurements may be insufficient to detect some forms of hypertension. For example, hypertension can occur in a pattern that evades detection via isolated office blood pressure measurement. Common hypertension patterns include white coat hypertension (elevated only during a limited morning period of time), borderline hypertension (fluctuating above and below definitional levels over time), nocturnal hypertension (elevated only during sleeping hours), isolated systolic hypertension (elevated systolic pressure with non-elevated diastolic pressure), and isolated diastolic hypertension (elevated diastolic pressure with non-elevated systolic pressure). To detect such hypertension patterns, it may be necessary to perform additional blood pressure measurements over time to obtain a more complete view of a person's blood pressure characteristics. Although continuous measurement of blood pressure can be achieved by invasive means, for example, via an intra-arterial pressure sensing catheter, noninvasive blood pressure measurement approaches are more typically used.

Current noninvasive blood pressure measurement approaches include ambulatory and home blood pressure measurement strategies. These strategies provide such a more complete view of a person's blood pressure characteristics and are often employed in recommended situations. Ambulatory blood pressure measurement is performed while the person performs daily life activities. Currently, ambulatory blood pressure measurements are typically performed every 20 to 30 minutes using brachial oscillometric blood pressure measurement cuffs. Ambulatory blood pressure measurement may be recommended where there is large variability in office blood pressure measurements, where a high office blood pressure measurement is made in a person with otherwise low cardiovascular risk, when office and home blood pressure measurements vary, where resistance to drug treatment of blood pressure is noted or suspected, where hypotensive episodes are suspected, or where pre-clampsia is suspected in pregnant women. Home blood pressure measurement includes isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

Current ambulatory and home blood pressure measurement approaches, however, fail to provide continuous measurement of blood pressure. Additionally, when an oscillometric blood pressure measurement cuff is used to monitor a person's blood pressure when sleeping, the intermittent inflation and deflation of the cuff can disturb the person's sleeping pattern, thereby harming the subject to some extent and potentially changing the person's sleeping blood pressure. Thus, convenient and effective approaches for noninvasive continuous measurement of blood pressure remain of interest.

According to the theory of arterial tonometry, the pressure in a superficial artery with sufficient bony support, such as the radial artery, may be accurately recorded during an applanation sweep when the transmural pressure equals zero. An applanation sweep refers to a time period during which pressure over the artery is varied from overcompression to undercompression or vice versa. At the onset of a decreasing applanation sweep, the artery is overcompressed into an occluded state, so that pressure pulses are not recorded. At the end of the sweep, the artery is undercompressed, so that minimum amplitude pressure pulses are recorded. Within the sweep, it is assumed that an applanation occurs where the arterial wall is flattened and transmural pressure turns to zero, and the arterial pressure is perpendicular to the surface and is the only pressure detected by a tonometer sensor.

FIG. 1 illustrates a method of measuring blood pressure using applanation tonometry. Here, a pressure transducer 1 is urged against the skin 2 of a user with an applanation force 3. The applanation force 3 and pressure transducer 1 applanate the target artery 4 such that the arterial wall tension 5 is parallel to the pressure transducer surface 6 and the arterial pressure 7 is perpendicular to the surface 6. Where the target artery 4 is applanated in such a manner, the arterial pressure may be measured by transducer 1. The target artery 4 may be supported by bone 8 and adjacent muscle 9. The target artery 4 may be the radial artery of the user and the bone 8 may be the radial bone.

FIG. 2 illustrates an exemplary cross-section of a wrist. As mentioned above, the radial artery is generally targeted in arterial applanation tonometry given its position adjacent the radial bone (radius). However, finding an ideal or preferred location for applanation of the radial artery can be difficult given its relative size. Compounding this problem is the fact that human anatomy varies from person to person and may change based on a person's height, weight, gender, etc. Accordingly, targeting the radial artery and identifying a preferred applanation location and orientation can be a challenge.

Some prior devices and methods have used a single pressure sensor for applanation of the target artery. Such methods and devices, however, require first locating a desired applanation location and then positioning of a pressure sensor at the desired location. As discussed above, this may not be a simple task given the size of the target artery and the variation in body anatomies. Further, some prior designs and methods have also required the use of wrist harnesses which orient the user's wrist in a preferred orientation prior to applying a pressure sensor to the target artery. These harnesses are bulky and inconvenient. Additionally many of the prior devices and methods require the assistance of a trained health care technician or are otherwise carried out in a clinic setting. Such devices and methods are inapplicable for day-to-day use by the general public.

In addition, given the complex anatomy of the wrist, as illustrated in FIG. 2, issues with signal processing and calibration have been challenging. While prior devices and methods have obtained pressure signals from patients, it has been challenging to convert these pressure signals into meaningful data. This may be further complicated if, as discussed above, the pressure sensor is applied to a less than ideal position where the sensor is not over the target artery or applied at an orientation where the pressure signal is not perpendicular to the surface of the sensor.

Accordingly, while applanation tonometry devices and methods have been provided, improvements in continuous and/or non-invasive blood pressure monitoring may be still be desired. For example, methods and devices for easily identifying a preferred applanation region and ensuring at least one pressure sensor is preferably placed adjacent the target artery may be of interest. These methods and devices may reduce issues with signal processing as a preferred applanation location may be identified and at least one pressure sensor is preferably placed such that a received pressure signal may be stronger and may require less processing. Further, identification of the preferred location may be carried out autonomously or may be identified by interpreting pressure signals from a plurality of locations. Pressures signals may be received from each location or region about the target artery selectively, simultaneously, sequentially, in subsets or the like. Further methods and devices that provide a convenient manner and/or less bulky device for measuring or monitoring blood pressure may increase the adoption of such techniques and may facilitate an increase in non-clinic setting measurements and monitoring of blood pressure.

SUMMARY OF THE INVENTION

The present invention provides non-invasive devices and methods for determining an absolute pressure of blood within a cardiovascular system of a user, the cardiovascular system including a heart and the user having a wrist covered by skin. More particularly, the present invention provides applanation tonometry methods and devices configured to non-invasively engage the skin on the wrist of the user for directly sensing an absolute blood pressure from the cardiovascular system of the user. In many embodiments, the devices and methods may be carried out without the requirement for periodic calibrations. Generally, approaches disclosed herein may passively track blood pressure values without any interaction required on the part of the user and/or may allow for on-demand or point measurements of blood pressure values by having a user move the arm on which the wrist device is worn.

In some aspects of the present invention, a wrist-worn device for non-invasively calculating an absolute arterial blood pressure may be provided. The wrist-worn device may include an elongate band configured to be coupled to a wrist of a user. A plurality of actuators may be coupled with the elongate band and configured to apply a variable pressure at a radial artery of the wrist. A pressure sensor array may be coupled with the plurality of actuators and configured to contact an underside of a wrist skin surface. The pressure sensor array may include a plurality of pressure sensors each being coupled with at least one of the plurality of actuators. The plurality of pressure actuators may be configured to be selectively actuated such that subsets of the pressure actuators are actuated to urge subsets of the plurality of pressure sensors against the wrist at a given time. A plurality of pressure measurements from the plurality of pressure sensors may be analyzed to identify a maximum pressure pulse within the plurality of pressure measurements and to calculate an absolute arterial pressure. In many embodiments an indication associated with the calculated absolute arterial pressure may be outputted to the user.

In some embodiments, the pressure actuators may be individually actuated so as to urge a single pressure sensor against the wrist at a time. The actuators may be a linear solenoid piston. Optionally, the plurality of actuators may be fluid bladders configured to be selectively filled with a fluid to drive a coupled pressure sensor against the wrist with a desired amount of pressure. The bladders may also be selectively deflated to reduce an amount of pressure applied by the coupled pressure sensor against the wrist. In some embodiments, the fluid bladders may be selectively filled using a phase change of a fluid from a liquid to a gas. In some embodiments, the bladder may also be inflated and deflated using micro-piezoelectric pumps.

In some embodiments, a bladder pressure sensor may be provided to identify a pressure within one or more of the plurality of fluid bladders. In some embodiments the plurality of pressure sensors comprise a piezoelectric film pressure sensor. The device may identify the absolute arterial blood pressure from piezoelectric film pressure measurements by calibrating the piezoelectric film pressure measurements with the pressure identified within one or more of the plurality of fluid bladders using the bladder pressure sensor.

Optionally the plurality of pressure sensors may include a piezoresistive pressure sensor. In some embodiments, the pressure sensor array may be a 12×1 array of pressure sensors or greater. In some embodiments, the pressure sensor array may be a 3×4 array of pressure sensors or greater. In some embodiments, the device may include a plurality of arrays (e.g., two or more 12×1 arrays, two or more 3×4 arrays, etc.). In many embodiments, the device may calculate the absolute arterial blood pressure without user interaction or periodic calibration.

In further aspects of the present invention, a method of measuring blood pressure with a wrist-worn device is provided. The wrist-worn device may have a plurality of pressure sensors that may be selectively urged against a wrist of a user using a plurality of actuators. Each of the plurality of pressure sensors may be coupled with at least one of the plurality of actuators. The method may include selectively urging a first pressure sensor of the plurality of pressure sensors against the wrist of the user at a first location with a first actuator and receiving a first pressure signal from the first pressure sensor. A second pressure sensor of the plurality of pressure sensors may be urged against the wrist of the user at a second location with a second actuator and a second pressure signal may be received from the second pressure sensor. A preferred pressure sensor may be identified between the first pressure sensor and the second pressure sensor and a preferred location on the wrist between the first location and the second location may be identified. The preferred pressure sensor and preferred location on the wrist may be identified by comparing the first pressure signal and the second pressure signal. A pressure signal from the preferred pressure sensor at the preferred location may then be outputted.

In some embodiments the first pressure sensor may be urged against the wrist of the user concurrently while the first pressure signal from the first pressure sensor is received so that the first pressure signal is a first swept pressure signal comprising a plurality of pressure waveforms measured while an applied pressure by the first actuator is varied. Similarly, the second pressure sensor may be urged against the wrist of the user concurrently while the second pressure signal from the second pressure sensor is received so that the second pressure signal is a second swept pressure signal comprising a plurality of pressure waveforms measured while an applied pressure by the second actuator is varied.

The first pressure signal and the second pressure signal may be compared by identifying a first maximum pressure pulse in the first swept pressure signal and a second maximum pressure pulse in the second swept pressure signal. A preferred pressure sensor may be associated with the pressure signal with a larger maximum pressure pulse amplitude. In some embodiments, the first pressure sensor is withdrawn from the wrist of the user by withdrawing the first actuator prior to receiving the second pressure signal from the second pressure sensor.

In further embodiments, a wrist-worn device for non-invasively measuring blood pressure of a user may be provided. The device may include a band to be worn proximate to a wrist of the user. A fluid bladder may be supported by the band. A piezoelectric film or piezoresistive pressure sensor may be coupled to a distal face of the fluid bladder to measure a pressure at the wrist. A bladder pressure sensor may be included for measuring a fluid pressure within the bladder. The fluid bladder may be configured to selectively inflate to urge the pressure sensor against the wrist of the user and to deflate to reduce a pressure applied against the wrist of the user. The fluid pressure signal from the bladder pressure sensor may be used to measure static pressure at the wrist while the pressure signal from the piezoelectric film or piezoresistive pressure sensor measures dynamic pressure at the wrist.

In some embodiments, the pressure transducer may include an array of pressure sensors. The fluid bladder may be an accordion fluid bladder. A driver may be disposed between the fluid bladder and the piezoelectric film pressure sensor. The driver may be configured to evenly distribution pressure from the fluid bladder across the pressure sensor.

In yet another aspect of the present invention. A method for non-invasively measuring blood pressure with a wrist-based pressure sensor is provided. The method may include receiving a swept pressure signal from at least one pressure sensor coupled to the wrist of a user. The swept pressure signal may include a plurality of pulse waveforms as the pressure transducer is moved from a first height to a second height relative to a heart of a user. A maximum pressure pulse may be identified in the swept pressure signal based on an amplitude associated with each of the plurality of pulse waveforms of the swept pressure signal A mean arterial pressure for the user may be calculated based on the identified maximum pressure pulse in the swept pressure signal and a height of the pressure sensor relative to the heart that is associated with the maximum pressure pulse. An indication may be outputted to the user that is associated with the calculated mean arterial pressure.

In some embodiments, the indication may be transmitted to a display on a wrist-worn device or mobile device of the subject. The pressure sensor may be at least one of a capacitive transducer, a piezoelectric film sensor, and a piezoresistive sensor. The pulse waveform associated with the highest amplitude out of the plurality of pulse wave forms may be the maximum pressure pulse. The height of the pressure sensor relative to the heart that is associated with the maximum pressure pulse may be received from a user input.

In some embodiments a signal may be received from an accelerometer coupled with the pressure sensor. The signal may be associated with an angle of the pressure sensor. The height of the pressure sensor relative to the heart that is associated with the maximum pressure pulse may be calculated by identifying an angle of the pressure sensor that is associated with the maximum pressure pulse and calculating the height of the pressure sensor relative to the heart based on the identified angle of the pressure sensor and a shoulder-to-wrist length of the user.

The shoulder-to-wrist length and a user heart height may be received from a user input. In some embodiments the shoulder-to-wrist length and a user heart height may be estimated using a user inputted height, gender, age, and/or weight and anthropometric dimensional data.

In some embodiments, the mean arterial pressure for the user may be calculated by calculating a hydrostatic pressure experienced at a radial artery of the user at the height of the pressure sensor relative to the heart that is associated with the maximum pressure pulse.

In some embodiments, the method may include applying a constant pressure at a radial artery of the wrist of the user with the pressure sensor. The constant pressure may be applied by actuating a subset of a plurality of actuators positioned behind the at least one pressure sensor to urge the at least one pressure sensor against the radial artery. A constant pressure may be applied at the radial artery of the wrist of the user by actuating a fluid bladder to force the pressure sensor against the radial artery. A driver may be positioned between the fluid bladder and the sensor and be configured to distribute pressure from the actuation of the fluid bladder evenly along the sensor. The constant pressure may be applied at the radial artery of the wrist of the user by actuating an accordion fluid bladder.

In further aspects, a device for measuring blood pressure of a user having a wrist and a heart, the wrist having an outer surface defined by skin, is provided. The device may include an elongate band configured to extend around the wrist of the user so as to support the device in engagement with the skin of the wrist. A sensor system may be supported by the elongate band with a sensor surface extending along the skin of the wrist when in use. A signal processing system may be coupled with the sensor system such that, in use, the signal processing system is configured to receive a swept pressure signal from the sensor system, the swept pressure signal comprising a plurality of pulse waveforms as the pressure sensor is moved from a first height to a second height relative to the heart of the user, each of the pulse waveforms having an associated amplitude and an associated height of the pressure sensor relative to the heart. The signal processing system may further identify a maximum pressure pulse in the swept pressure signal in response to the amplitudes of the pulse waveforms of the swept pressure signal; and calculate a mean arterial pressure for the user based on the identified maximum pressure pulse and the associated height of the pressure sensor relative to the heart of the maximum pressure pulse. A signal indicative of a pressure of the blood pressure of the user may be outputted in response to the sensor signals.

In additional aspects of the present invention, a method of measuring blood pressure of a user having a wrist, skin defining an outer surface of the wrist, may be provided. The method may include maintaining engagement between the skin of the wrist and a film pressure sensor of a wrist-worn device using a band extending around the wrist, where the wrist-worn device may have a fluid bladder and a film pressure sensor. The fluid bladder may be coupled with a fluid bladder pressure sensor. The method may include inflating the fluid bladder to urge against the wrist of the user and receiving a film pressure sensor signal associated with a pressure of engagement between the fluid bladder and the wrist. A fluid bladder pressure signal may be received from the fluid bladder pressure sensor—the fluid bladder pressure signal may be associated with a pressure in the fluid bladder. Thereafter, the film pressure signal from the film pressure sensor may be calibrated with the fluid bladder pressure signal so that the film pressure signal indicates dynamic pressure at the wrist while another pressure may measure the bladder static pressure. A blood pressure of the user may be determined based on the calibrated film pressure signal and an indication of the determined blood pressure of the user may then be outputted.

In yet further aspects, a wrist-worn device for non-invasively measuring blood pressure of a user may be provided. The device may include a band to be worn around a wrist of the user. The band may define an inner face oriented toward the wrist in use and an outer face oriented away from the wrist. A fluid bladder may be supported by the band and a film pressure sensor may be supported along an inner face of the fluid bladder to measure a pressure of engagement between the bladder and the wrist. A bladder pressure sensor for measuring a fluid pressure within the bladder may be provided. And, a processor may be coupled to the film pressure sensor and the bladder pressure sensor. The processor may be configured so that, when the fluid bladder is inflated to urge the film pressure sensor against the wrist of the user and deflated to reduce a pressure applied against the wrist of the user, the fluid pressure signal from the bladder pressure sensor may be used for measuring static pressure and the film pressure sensor may be used for measuring dynamic pressure at the wrist.

Additionally, a method for measuring blood pressure of a user having a wrist and a heart, the wrist having an outer surface defined by skin, may be provided. The method may include receiving a swept pressure signal from at least one pressure sensor coupled to the wrist of the user. The swept pressure signal may include a plurality of pulse waveforms as the pressure sensor is moved from a first height to a second height relative to the heart of the user. Each of the pulse waveforms may have an associated amplitude and an associated height of the pressure sensor relative to the heart. A maximum pressure pulse in the swept pressure signal may be identified in response to the amplitudes of the pulse waveforms of the swept pressure signal. A mean arterial pressure for the user may be identified based on the identified maximum pressure pulse and the associated height of the pressure sensor relative to the heart of the maximum pressure pulse. The method may further include outputting an indication of the blood pressure in response to the calculated mean arterial pressure.

In yet another aspect, a device for determining blood pressure of a user having a wrist, skin defining an outer surface of the wrist and an artery, may be provided. The device may include an elongate band configured to extend around the wrist of the user so as to support a skin interface surface of the device in engagement with the skin of the wrist. A plurality of pressure actuators may couple the elongate band to the skin interface surface. The pressure actuators may be configured to apply a variable pressure between the skin interface surface and the skin of the wrist at an array of regions distributed along the skin interface surface. A sensor system with a sensor surface may extend along the skin interface surface. A signal processing system may be coupled with the sensor system and the actuators such that, in use, first and second subsets of the pressure actuators selectively and sequentially urge associated first and second subsets of the array against the wrist so as to generate a plurality of sensor signals from the sensor system. The signal processing system may be configured to output a signal indicative of a pressure of the blood pressure of the user in response to the sensor signals.

A method of measuring blood pressure of a user may also be provided where the method includes maintaining engagement between the skin of the wrist and a skin interface of a wrist-worn device using a band extending about the wrist, where the wrist-worn device may have a plurality of actuators and a sensor system. The skin interface may include an array of surface regions. The method may further include selectively urging a first region of the array against the wrist with a first actuator and receiving a first associated signal from the sensor system and selectively urging a second region of the array against the wrist with a second actuator and receiving a second associated signal from the sensor system. A preferred subset of the array may be identified by comparing the first signal and the second signal. A pressure signal indicative of a pressure of blood of the user may be derived using signals associated with the preferred subset of the array and the pressure signal may be outputted.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The invention will be better understood on reading the following description and examining the figures that accompany it. These figures are provided by way of illustration only and are in no way limiting on the invention.

BRIEF DESCRIPTION OF THE DRAWINGS

FIG. 16 illustrates the selective actuation of a single region of a skin interface 210 against a wrist of a user according to embodiments of the present invention;

FIG. 17 illustrates device selectively actuating a subset of regions of a skin interface against a wrist of the user according to embodiments of the present invention:

FIG. 18 illustrates a device that includes a pressure film sensor that may be coupled with one of a plurality of actuators;

FIG. 19 illustrates device selectively actuating a subset of regions of a skin interface and pressure film sensor against a wrist of the user according to embodiments of the present invention;

DETAILED DESCRIPTION

The present invention generally relates to blood pressure monitoring. In some embodiments, methods and devices of measuring a mean arterial pressure are provided and/or monitoring blood pressure changes. A wrist-worn device may include one or more sensors backed by a plurality of actuators. Subsets of the plurality of actuators may be selectively actuateable against a wrist of a user for urging a subset of the sensors against a wrist of the user or a portion of a pressure sensor film against the wrist. A preferred sensor and location may be identified based on pressure signals received from each of the sensors and sensor locations. In some embodiments, devices may use a fluid bladder coupled with piezoelectric film sensors. A fluid bladder pressure sensor may be used to measure the static pressure at the wrist and the piezoelectric film signal may provide a dynamic pressure reading. In yet another embodiment, a mean arterial pressure may be calculated by processing a swept pressure signal obtained as a pressure sensor is swept through different heights.

Figure 3:
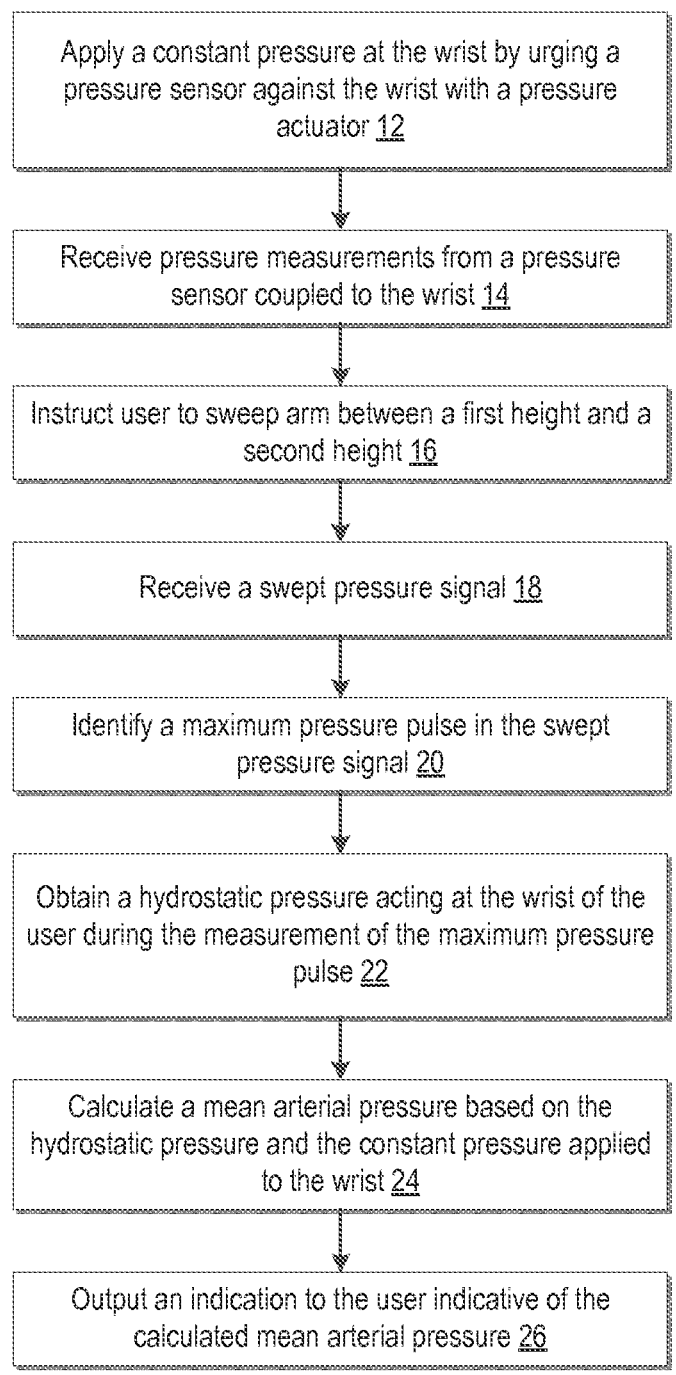
FIG. 3 illustrates a method for calculating a mean arterial pressure of a user according to embodiments of the present invention.

FIG. 3 illustrates an exemplary method 10 for calculating a mean arterial pressure with a wrist-worn pressure sensor. At step 10, after the wrist-worn device is coupled with a user's wrist, a constant pressure may be applied to the wrist with a pressure sensor coupled with a pressure actuator. Pressure measurements from the wrist may be received from the pressure sensor once it is urged against the wrist 14. The user may then be instructed to sweep their arm between a first height and a second height 16 to vary the hydrostatic pressure experienced at the wrist. As the user sweeps their arm from the first height to the second height, a swept pressure signal may be received from the pressure sensor where the pressure pulses vary in amplitude due to the changes in hydrostatic pressure experienced at the wrist as the user moves their arm. The swept pressure signal may be analyzed to identify a maximum pressure pulse in the swept pressure signal 20. A hydrostatic pressure associated with the maximum pressure pulse is obtained 22 after identifying the maximum pressure pulse. A mean arterial pressure may then be calculated 24 based on the obtained hydrostatic pressure and the constant pressure applied to the wrist. An indication may then be outputted 26 to provide a user an indication of the obtained mean arterial pressure.

The exemplary method 10 utilizes the changes in hydrostatic pressure for applanation of an artery of the user. In many embodiments, the method 10 may be used for applanation of the radial artery or other superficial artery with sufficient bony support of a user. As the wrist changes in height relative to the heart of the user, the amount of hydrostatic pressure will vary and apply different amounts of pressure at the wrist of the user for applanation of the target artery. This exemplary method 10 for calculating mean arterial pressure is counterintuitive as many prior non-invasive methods of measuring and monitoring blood pressure teach away from arm movement during blood pressure monitoring. More specifically, many prior methods require or suggest that a user maintain their arm in preferred position throughout the measurement and/or monitoring of the user's blood pressure. Further, some methods of monitoring or measuring blood pressure may require wrist harnesses that lock the user's wrist in a preferred orientation while the measurements are taken. A method where the user may obtain blood pressure measurements and/or monitoring without the need for bulky wrist harnesses may provide a more convenient method in which users can easily measure their own arterial pressure on the go and outside of a clinic setting.

In many embodiments, after the user has coupled the device to their wrist, a constant pressure may be applied 12 by urging a pressure sensor against the wrist of the user. The constant pressure may be applied by a number of different ways. For example, wrist-worn device straps may be manually tightened (e.g., a Velcro strap, adjustable strap, or the like etc.) or mechanically tightened (e.g., through a ratcheting mechanism, or the like, etc.). The straps can be tightened using micro-linear actuator, or electroactive polymer (artificial muscles) In many embodiments a pressure actuator may be used to urge the pressure sensor against the wrist of the user. For example, solenoids, linear actuators, fluid bladders or the like may be coupled with a pressure sensor and actuated to urge the pressure sensor against the wrist and may also be actuated to reduce an amount of pressure applied.

In some embodiments, the applied constant pressure could be selected in the range 80-120 mmHg, which is close to the range of mean arterial pressures of interest. The use of applanation tonometry to determine mean arterial pressure requires that the transmural pressure equals zero, P_transmural=0. The transmural pressure acting across an arterial wall is defined as the difference between the internal pressure and external pressure, P_transmural=P_internal−P_external. Under the assumption of negligible resistance from the aorta to large peripheral arteries, the internal pressure P_internal at a peripheral artery is the sum of the central aortic blood pressure and the hydrostatic pressure at the peripheral artery relative to the aorta. Hence, the internal pressure of a peripheral artery that is below the aorta is greater than the blood pressure of the aorta; similarly, the internal pressure of a peripheral artery that is above the aorta is less than the blood pressure of the aorta. For a constant external pressure, the transmural pressure is largest when the peripheral artery is at its lowest point and smallest when the peripheral artery is at its highest point. When the artery is at its lowest point, the transmural pressure is typically greater than zero. As the artery is raised from its lowest point, the transmural pressure decreases until it reaches zero and begins to become negative. It follows that for a constant external pressure P_external, the transmural pressure will reach zero at a height that depends on the central aortic blood pressure. As the central aortic blood pressure increases, the transmural pressure equals zero at increasing peripheral artery heights. Conversely, as the central aortic blood pressure decreases, the transmural pressure equals zero at decreasing peripheral artery heights. For example, a constant pressure may be applied at the wrist such that transmural pressure at the wrist is positive when the user's arm is at a resting position (e.g., by the user's side when standing). The constant pressure may also be configured to allow the transmural pressure to turn negative after the user raises their arm a height relative to the user's heart. With such a configuration, an applanation of a target artery where the arterial wall is flattened and transmural pressure turns to zero. Here, the arterial pressure is perpendicular to the surface may occur at a height between the resting position where transmural pressure is positive and the raised position where transmural pressure is negative. At the this height of the wrist, the hydrostatic pressure acting on the user's wrist and the constant pressure applied at the wrist may applanate the artery such that the arterial pressure is the only pressure detected by the pressure sensor (e.g., a desired applanation).

Figure 21:
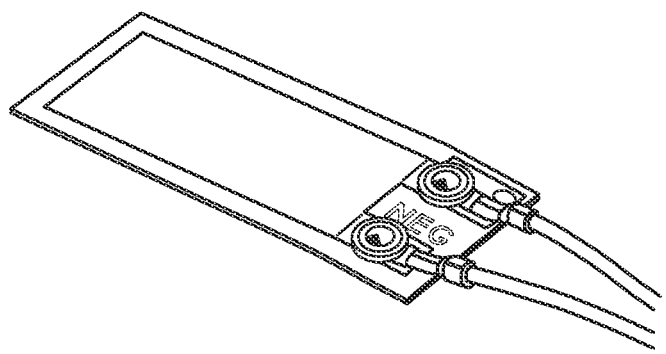
FIG. 21 shows an exemplary piezoelectric film sensor that may be used with embodiments of the present invention described herein.
Figure 22:
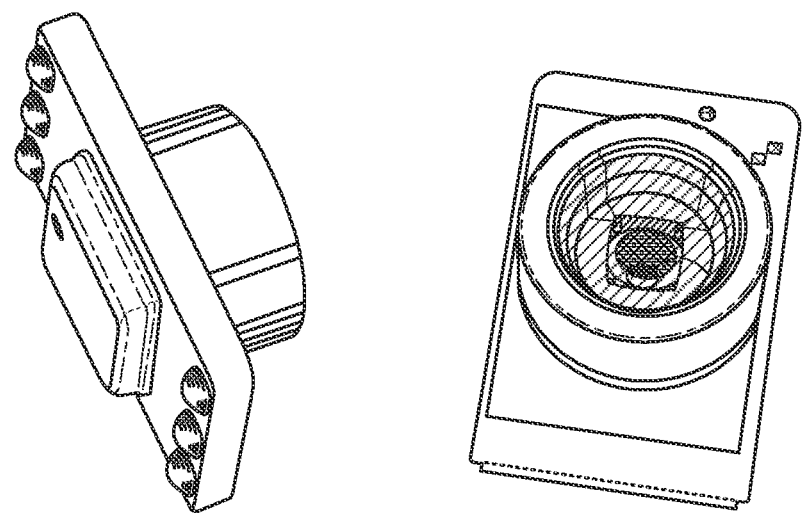
FIG. 22 shows an exemplary piezoresistive pressure sensor that may be used with embodiments of the present invention described herein.

Once the pressure sensor is coupled with the wrist of the user, a pressure signal/measurement may be received from the pressure sensor 14. The received pressure signal may correspond to an arterial pressure of the user. In some embodiments, the pressure sensor may be a capacitive pressure sensor, a piezoelectric film pressure sensor, a piezoresistive microelectromechanical system (MEMS) pressure sensor, bladder fluid or gas pressure sensor, or the like. FIG. 21 shows an exemplary piezoelectric film sensor that may be used with embodiments of the present invention described herein. FIG. 22 shows an exemplary piezoresistive pressure sensor that may be used with embodiments of the present invention described herein.

In some embodiments a piezoelectric film pressure sensor may be preferable as the film may be thin and may better conform to the contours of the user's wrists. When using a piezoelectric film pressure sensor, some embodiments may actuate the piezoelectric film pressure sensor with a fluid bladder. A fluid bladder pressure sensor identifying an applied pressure by the fluid bladder may be used to measure static pressure while the piezoelectric film pressure sensor measures dynamic pressure. The piezoelectric film measures the dynamic pressure oscillations from the artery, while the fluid bladder pressure sensor measures the static applied pressure from the fluid bladder.

In some embodiments a piezoresistive may be preferable as the film may also conform to the contours of the user's wrist and may further measure a static and dynamic pressure.

In many embodiments, an array of pressure sensors may be used to ensure that at least one of the pressure sensors of the array is positioned at a preferable location relative the target artery of the user. For example, in some embodiments, a 12×1 array, two 12×1 arrays, a 3×4 array, two 3×4 arrays, or the like of pressure sensors may be applied transverse to the radial artery of the wrist. In some embodiments, a single pressure actuator may be used to urge the entire array of sensors against the target artery. In other embodiments, multiple pressure actuators may be used to urge portions of the array of sensors against the target artery. For example, some embodiments of the wrist-worn device may have each pressure sensor coupled with a pressure actuator such that each individual pressure sensor may be individually urged against and away from the wrist by a desired amount and at different times. Further details of exemplary devices are discussed further below.

The user may be instructed to sweep their arm between a first height and a second height 16. The first height and second heights may be, for example, a resting position where the user's arm rests against their side when standing and a raised position where the user's arm is raised above their head. In many embodiments, it may be preferable to instruct that the user slowly sweep their hand to different heights so that a plurality of pressure pulses may be measured at different heights. Further, while not essential, it may be preferable to instruct the user to maintain their arm in an extended position or straight orientation (e.g., where the elbow is locked) so that a wrist height measurement, relative to the user's shoulder, may be calculated using an angle of the arm and a shoulder-to-wrist length.

As the user moves their arm to different heights, a swept pressure signal may be received 18. The swept pressure signal may include a plurality of pressure pulses that vary in amplitude due to changing hydrostatic pressure experienced at the wrist at the different heights.

As discussed above, a desired applanation of a target artery where the arterial wall is flattened and the arterial pressure is perpendicular to the surface may occur at a desired height between the first wrist height (e.g., resting position where arm is positioned by the user's side) where the transmural pressure is positive and a second wrist height (e.g., a raised position above the resting position) where the transmural pressure is negative or vice-versa. At this desired height where the transmural pressure is zero, the hydrostatic pressure acting on the user's wrist and the constant pressure applied at the wrist may applanate the artery such that the arterial pressure stress is measured by the pressure sensor. Accordingly, in a height swept pressure signal with a plurality of pressure pulses measured at different heights, the desired applanation of the target artery is associated with the pressure pulse with the largest amplitude (i.e., "maximum pressure pulse"). Thus, after receiving the swept pressure signal 18, a maximum pressure pulse in the swept pressure signal is identified 20 as it is associated with the desired applanation of the target artery and a corresponding hand height, location, and/or orientation may be recorded for calculating a hydrostatic pressure.

To calculate a mean arterial pressure 24, the applied constant pressure and a hydrostatic pressure acting on the wrist during the measurement of the maximum pressure pulse are obtained. The mean arterial pressure (MAP) maybe calculated by the following formula:

$$MAP = P_{applied} - P_{hydrostatic}, \quad (1)$$

where: $P_{applied}$ is the constant pressure applied at the wrist and $P_{hydrostatic}$ is the hydrostatic pressure acting on the wrist during the measurement of the maximum pressure pulse.

$P_{hydrostatic}$ may be calculated by:

$$P_{hydrostatic} = \rho g h, \quad (1a)$$

where: ρ is the density of blood, g is the gravitational constant, and h is the height difference between the heart and the wrist of the user ("heart-to-wrist height"). The average density of blood is approximately 1060 kg/m. The gravitational constant is approximately 9.8 m/s². The height difference, h, may be defined as:

$$h = Height_{heart} - Height_{wrist}, \quad (2)$$

Where h is obtained in centimeters (cm) and where MAP is outputted in mmHg, equation (1) may be rewritten to:

$$MAP(\text{mmHg}) = Pressure_{applied} - 0.78\left(\frac{\text{mmHg}}{\text{cm}}\right) * h(\text{cm}), \quad (3)$$

Accordingly, MAP may be calculated by obtaining the constant pressure applied at the wrist and by obtaining the heart-to-wrist height of the user that is associated with the measurement of the maximum pressure pulse.

Figure 4:
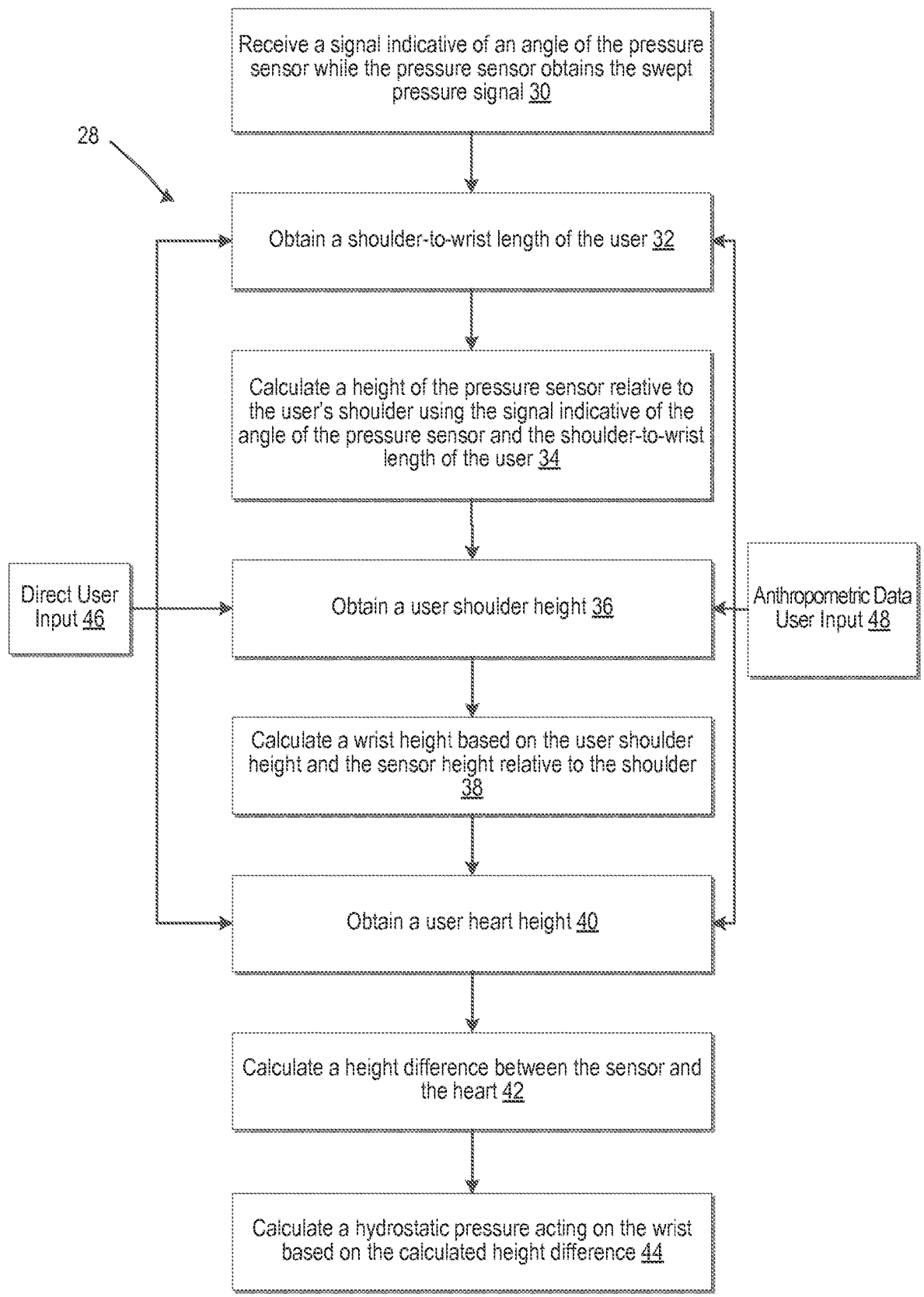
FIG. 4 illustrates a method for determining a hydrostatic pressure acting on the wrist of a user according to embodiments of the present invention.

FIG. 4 illustrates an exemplary method 28 of calculating the hydrostatic pressure at the wrist 22. At step 30, a signal indicative of an angle of the pressure sensor may be received while the pressure sensor obtains the swept pressure signal. A shoulder-to-wrist length of user may be obtained 32. A height of the sensor relative to the user's shoulder may be calculated 34 using the signal indicative of the angle of the pressure sensor and the obtained shoulder-to-wrist length. A height of the user's shoulder may then be obtained 36 for use in calculating a wrist height 38 based on the shoulder height and the sensor height relative to the shoulder. A user's heart height may then be obtained 40. A height difference between the pressure sensor/wrist and the heart may then be calculated 42 based on the obtained user heart height 40 and the calculated wrist height 38. Using the calculated height difference, a hydrostatic pressure acting on the wrist at the height of the sensor may be calculated 44 and used to calculate the MAP 24 (e.g., using equation 3).

In some embodiments, an accelerometer may be coupled with the wrist-worn device and may output an angle of the pressure sensor 30 while receiving the swept pressure signal. The received angle information 30 may be used with an obtained shoulder-to-wrist height 32 to identify a height of the pressure sensor and wrist of the user relative to the shoulder of the user. For example, a shoulder-to-wrist height ($Height_{shoulder-to-wrist}$) may be calculated with the following:

$$Height_{shoulder-to-wrist} = l_{shoulder-to-wrist} * \sin \theta_{wrist}; \quad (4)$$

where: $l_{shoulder-to-wrist}$ is the length of the shoulder to the wrist of the user, and theta is the angle of the wrist/pressure sensor relative to horizontal identified by the accelerometer.

Optionally, if the accelerometer returned an angle, sp, of the pressure sensor 30 relative to vertical (e.g., where an arm raised straight up returns an angle of 0° and an arm position straight down returns an angle of 180°), shoulder-to-wrist height may be calculated with the following:

$$Height_{shoulder-to-wrist} = l_{shoulder-to-wrist} * \cos \varphi_{wrist}. \quad (5)$$

The length of the shoulder to the wrist of the user may be obtained 32 directly from a user input 46 for use in equation (4) or (5). For example, a user interface may be provided that requests the user to input a shoulder-to-wrist length. In response to a user input indicative of the shoulder-to-wrist length, the device may store the received user input for use in equation (4) and/or (5).

In some embodiments of the invention, the user may input anthropometric data 48 and the length of the shoulder to the wrist of the user may be estimated based on the user inputted anthropometric data. For example, in some embodiments, a user may input a gender and a height. In further embodiments, other anthropometric data may be obtained such as a user's age, weight, ethnicity, etc. Based on received anthropometric data, shoulder-to-wrist length may be estimated. For example, in some embodiments, a shoulder-to-wrist length of a male user may be estimated as approximately 30%-36% of the user's inputted height, and in some embodiments preferably about 33%-34% of the user's inputted height and in further embodiments, even more preferably about 33.4%-33.5% of the user's inputted height. For some embodiments, a shoulder-to-wrist length of a female user may be estimated as approximately 31%-37% of the user's inputted height, and in some embodiments, even more preferably about 33/%-35% of the user's inputted height, and in further embodiments, even more preferably about 33.3%-34.5% of the user's inputted height.

Thereafter, a user's wrist height ($Height_{wrist}$) may be calculated 38 by obtaining a user shoulder height 36 with the following:

$$Height_{wrist} = Height_{shoulder} + Height_{shoulder-to-wrist} \quad (6)$$

Optionally, equation (6) may be substituted into equation (2) to provide:

$$h = Height_{heart-wrist} = Height_{heart} - (Height_{shoulder} + Height_{shoulder-to-wrist}). \quad (7)$$

In a similar manner to receiving a shoulder to wrist length, a shoulder height may be requested and received through a user input 46 or may be estimated using received anthropometric data 48. For example, in some embodiments, a shoulder height of a male user may be estimated as approximately between 80%-84% of the user's height, and in further embodiments, preferably between about 81.5%-82.5% of the user's height, and even more preferably about 81.9%-82% of the users height. For a female user, a shoulder height may be estimated as approximately between 81.5%-83.5% of the user's inputted height, and in further embodiments, preferably between 82%-83% of the user's inputted height, and even more preferably about 82.4%-82.6% of the user's inputted height.

To calculate for $Height_{heart-wrist}$ using equation (6) or equation (7), a user heart height 40 may be obtained directly through user input 42 (user inputted and stored for subsequent use) or may be estimated based on anthropometric data inputted by the user 50 (e.g., gender, height, or the like). In some embodiments, a height of the user's heart may be estimated as approximately 70-75% of the user inputted height, in further embodiments, preferably about 72%-73% of the user inputted height and even more preferably about 72.5% of the user inputted height.

Once Height$_{heart-wrist}$ is obtained, a hydrostatic pressure acting on the wrist may be calculated 44 using equation (1a) and a MAP may be calculated 24 using equation (3).

After calculating an MAP for a user, the method 10 may then proceed to output an indication to the user that is indicative of the calculated MAP 26. The output may comprise the calculated MAP. Alternatively, the output may be a general indicator that indicates where the calculated MAP falls on a spectrum (e.g., good MAP, intermediate MAP, bad MAP). The output may be audio (e.g., a voice or other audio indicator) or visual. For example, the output may be outputted to a display of the device or LEDs may be illuminated to provide the indication. In some embodiments, the output may be communicated to a separate wearable device coupled with the wrist-worn blood pressure monitoring device. For example, in some embodiments, the wrist-worn blood pressure monitoring device may be coupled with a separate wrist-worn electronics device. The separate device may include a separate power source, processor, communications port, memory, and inputs/outputs, etc. In further embodiments, the output may be transmitted (e.g., wirelessly) to a mobile device of a user. For example, an indication of the calculated MAP may be transmitted to a smartphone, or other portable electronic device (e.g., tablets, PDAs, laptops, or the like) for recordation, analysis, and documentation.

In some embodiments, the wrist-worn blood pressure monitor may output or otherwise transmit received sensor signals (e.g., wrist angle, pressure signal, swept pressure signal or the like) to a separate device for further processing and recordation. This may be advantageous in reducing the processing power needed in the wrist-worn device, thereby allowing the device to have a smaller footprint and may allow the device to be operated for longer periods of time due to a lower power consumption. Further, by transmitting the data to a secondary device (e.g., watch, phone, tablet, or the like) on-board storage and battery requirements may be reduced, thereby further allowing the device to have a smaller footprint.

While generally discussed as instructing the user to actively, intentionally, and/or knowingly carry out the arm sweep for generating the swept pressure pulse, other embodiments may be passive where the pressure signals may be received throughout a period of time as the user carries out daily activities. Other sensor data (e.g., accelerometer data) may indicate the movement of the sensor to different heights and may indicate the receipt of a swept pressure signal. The passively received swept pressure signal (e.g., where the user does not carry out the arm sweep in response to instructions), may then be analyzed for calculating a MAP of the user per the methods described above.

Optionally, in some embodiments, an accelerometer and gyroscope on the wrist could be used to trace the trajectory of the wrist during daily movements and, hence, determine the height between the wrist and the shoulder, the heart-to-wrist height can then be determined by a single measurement of the shoulder-to-heart height.

Figure 5C:
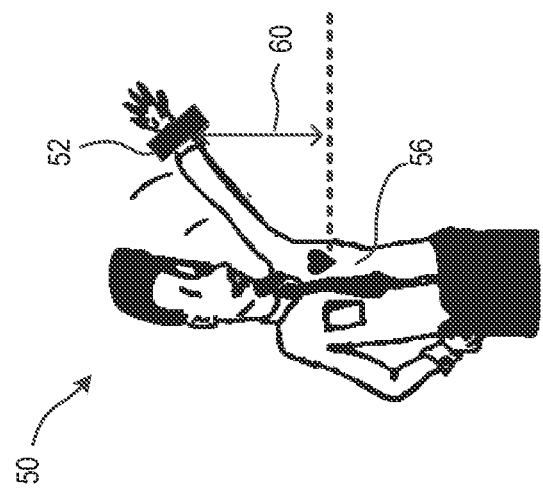
FIG. 5A-5C illustrate a method of changing the hydrostatic pressure at the wrist of the user according to embodiments of the present invention.
Figure 5B:
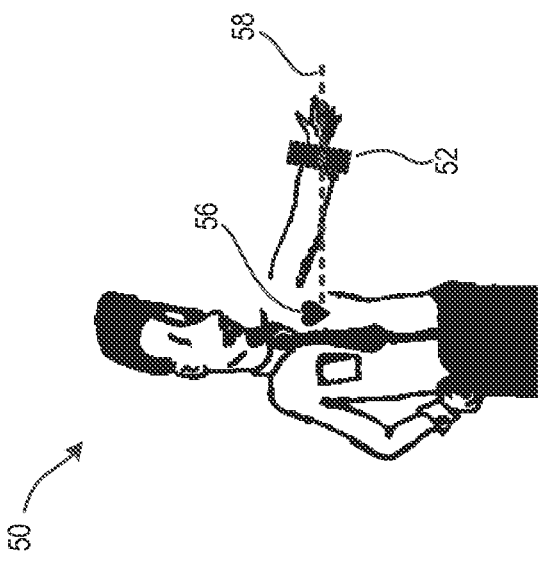
Figure 5A:
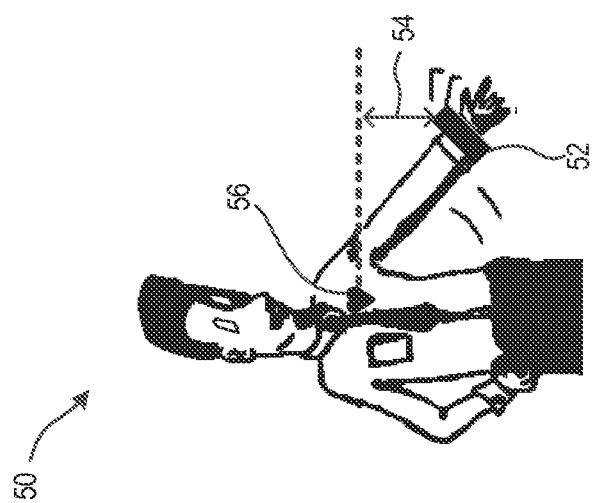

FIG. 5A-5C illustrate a user 50 sweeping his arm for producing the swept pressure signal for the exemplary method 10. FIG. 5A illustrates the user 50 with a wrist-worn device 52 at a first height 54 relative to his heart 56 where the wrist/wrist-worn device 52 is below the user's heart 56. FIG. 5B illustrates the user 50 with the wrist-worn device 52 at an height 58 where the wrist/wrist-worn device 52 is approximately equal to a height of his heart 56. FIG. 5C illustrates the user 50 with the wrist-worn device 52 at a second height 60 relative to his heart 56 where the wrist/wrist-worn device 52 is above the user's heart 56.

In FIG. 5A, Height$_{heart-wrist}$ has a positive value as the heart height is greater than the wrist height. Accordingly, per equation (1a), the user 50 experiences a positive hydrostatic pressure at the wrist when the wrist is below the heart 56 of the user. For example, using equation (1a), the user experiences +40 mmHg of hydrostatic pressure at the wrist when the wrist is about 51.28 cm below the heart 56. Thus if the desired applanation of the target artery (or a measurement of the maximum pressure pulse) occurs when the wrist is below the heart height 56, the calculated MAP is less than the applied pressure.

In FIG. 5B, Height$_{heart-wrist}$ is approximately zero. Accordingly, per equation (1a), at this height, no hydrostatic pressure acts on the wrist relative to the heart 56. If the desired applanation of the target artery (or a measurement of the maximum pressure pulse) occurs when the wrist height is equal to the heart height, the calculated MAP is equal to the applied pressure.

In FIG. 5C, Height$_{heart-wrist}$ has a negative value as the heart height is less than the wrist height, (see equation (2)). Accordingly, per equation (1a), the user 50 experiences a negative hydrostatic pressure at the wrist relative to the heart when the wrist is above the heart 56 of the user 50. For example, using equation (1a), the user experiences −40 mmHg of hydrostatic pressure at the wrist when the wrist is about 51.28 cm above the heart 56. If the desired applanation of the target artery (or a measurement of the maximum pressure pulse) occurs when the wrist is above the heart height 56, the calculated MAP is greater than the applied pressure.

In many embodiments, the transmural pressure at a low end of the arm sweep may be positive where the wrist and device are positioned below the heart (e.g., FIG. 5A) and may be negative at a high end of the arm sweep where the wrist and device are positioned above the heart (e.g., FIG. 5C). In such instances, the desired applanation of the target artery and measurement of the maximum pressure pulse will occur at an intermediate height between the low end of the arm sweep and the high end of the arm sweep where the transmural pressure is zero.

Figure 6:
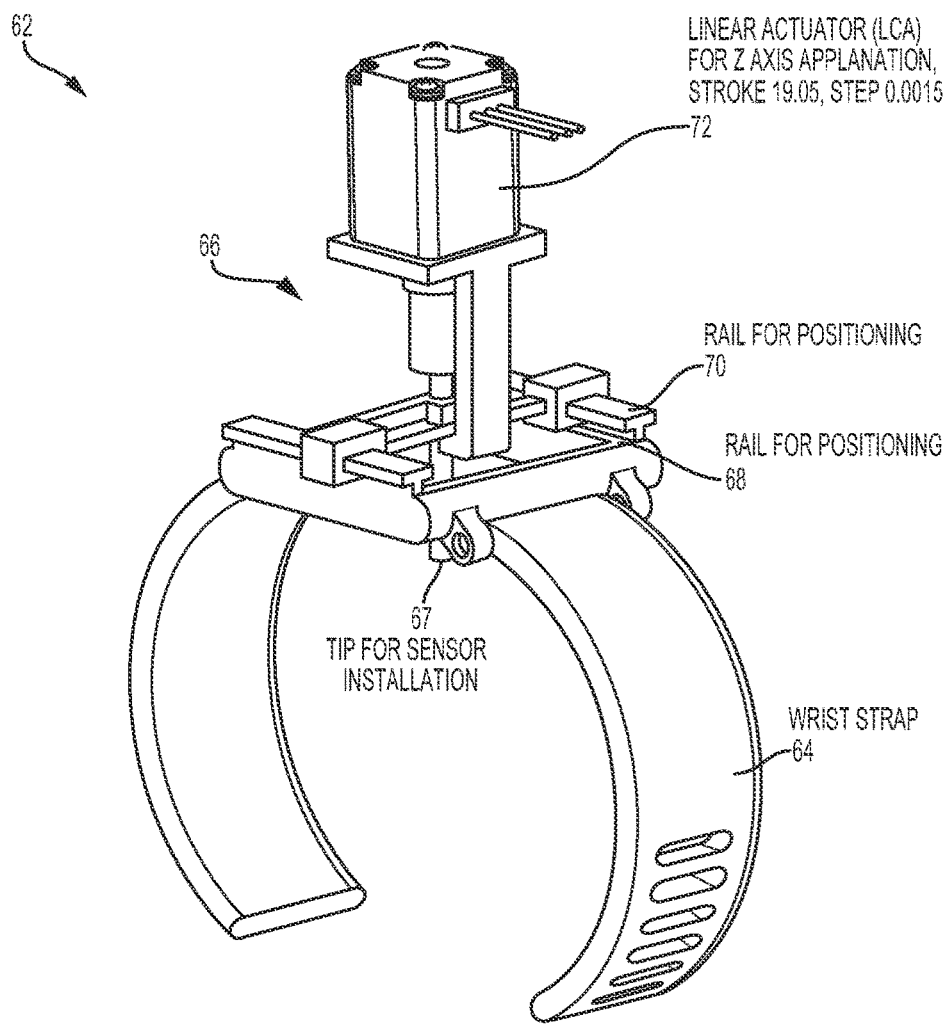
FIG. 6 illustrates a wrist-worn device for measuring pressure pulses at the wrist of the user according to embodiments of the present invention.

FIG. 6 shows an exemplary device 62 for monitoring and/or measuring blood pressure of a user. The device 62 may include a wrist strap 64 and an actuator system 66 supported by the wrist strap 64. The actuator system 66 may include a tip 67 for coupling with a pressure sensor (not shown) and may be configured to position the pressure sensor at a desired location relative to a coupled wrist.

The wrist strap 64 may be provided for coupling with a wrist of the user. While illustrated as configured to partially wrap around a user's wrists, other embodiments may fully wrap around a user's wrist. As discussed above, wrist strap 64 may be tightened around the wrist of a user to apply the constant pressure during an MAP measurement. The wrist strap 64 may include clasps, ratcheting mechanisms, or other engagement/tightening features for coupling and/or tightening the device 62 with a wrist of the user.

In some embodiments, the wrist strap 64 may be configured to couple with/modify a separate wearable device with a strap. For example, the wrist strap 64 may couple to the inner surface/contact surface of a strap of a separate wearable device. In some embodiments, the separate device may also be a wrist worn device, such as a watch or the like.

Actuator system 66 may be supported relative to a wrist of the user via wrist strap 64. The actuator system 66 may provide a number of degrees of freedom to a pressure sensor coupled a tip 67 of the actuator system 66 relative to the wrist so that a pressure sensor may be preferentially placed at a desired location on the wrist and with a desired amount of pressure. For example, as illustrated actuator system 66 includes a first rail 68 for positioning a coupled pressure sensor perpendicular or transverse to a coupled wrist of a user. Actuator system 66 may further include a second rail 70 for positioning the tip 67 along the length of a target artery. Further, actuator system 66 may include a linear actuator 72 for urging a pressure sensor coupled thereto against a wrist of a user (e.g., for applying the constant pressure for measuring MAP). In some embodiments, the 2 rail system can be replaced by an automatic step controlled linear stage positioning system. And the linear actuator 72 can be replaced with a voice coil actuator (VCA) or a piezoelectric stack actuator.

The exemplary device 62 may be configured to carry out the exemplary method 10. In some embodiments, the exemplary device 62 may be used to monitor blood pressure using applanation tonometry where the actuator 72 is configured to perform a pressure sweep in the Z direction (i.e. into the wrist) for identifying an MAP and then actuated to apply a preferred pressure so that the pressure sensor provides continuous blood pressure monitoring.

Figure 7:
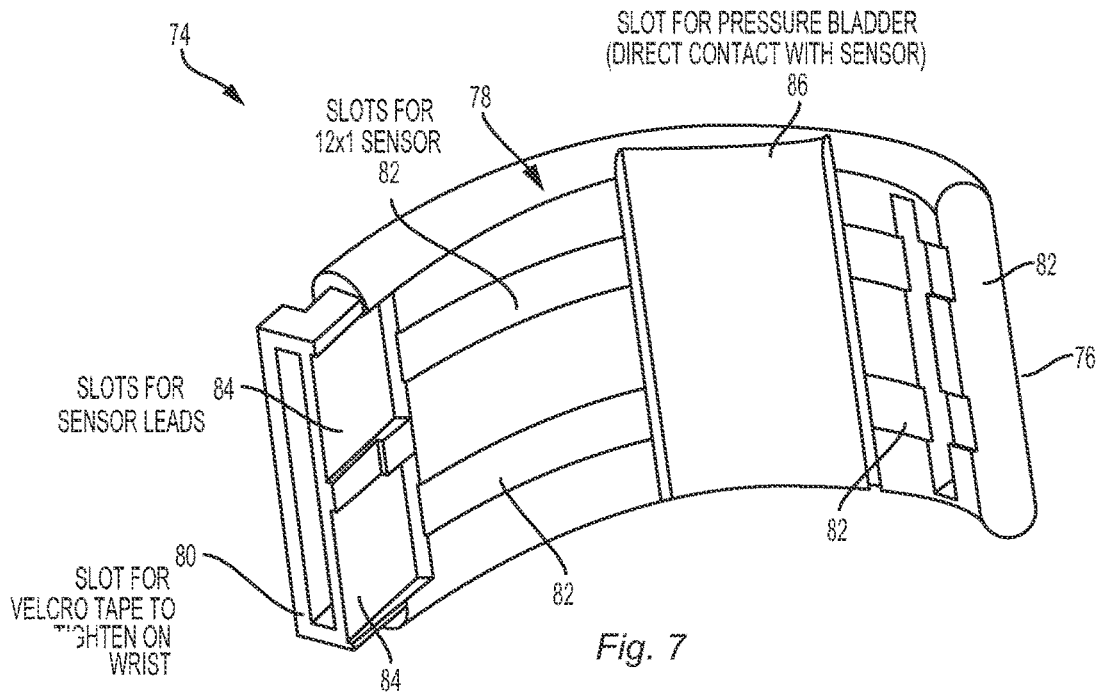
FIG. 7 illustrates another wrist-worn device for measuring pressure pulses at the wrist of the user according to embodiments of the present invention.

FIG. 7 illustrates another exemplary device 74 for monitoring and/or measuring blood pressure of a user. The device 74 may include a housing 76 with a curved configuration with an inner surface 78 configured to match the curvature of the underside of the wrist of a user. Housing 76 may include slots or engagement features 80 for coupling with a wrist strap (not shown). The housing 76 may include recessed surfaces/slots 82 for receiving a sensor array and corresponding recessed surfaces/slots 84 for receiving sensor leads of a received sensor array. Further, in some embodiments, housing 76 may include a recessed surface/slot 86 for receiving a pressure actuator for urging a received sensor array against a wrist of a user.

Slots 80 may be configured to receive a wrist strap for coupling the device 74 to a wrist of the user. The slot may, for example, receive a hook-and-loop fastener strap (e.g., Velcro) tape, or the like) for securing the device 74 to the wrist.

The recessed surface 82 may be configured for receiving a pressure sensor array. In some embodiments the pressure sensor array may comprise capacitive pressure sensors, piezoresistive MEMS pressure sensors, piezoelectric film pressure sensors, or the like. In some embodiments a 12×1 pressure sensor array may be received. The recessed surface 82 may align a received sensor array parallel with the wrist strap so that the sensor array traverses the target artery (e.g., radial artery). This may ensure that at least one of the pressure sensors of the pressure sensor array is positioned over the target artery. In the illustrated embodiment, two recessed surfaces 82 are provided for two 12×1 sensor arrays. While illustrated with two recessed surfaces 82 for receiving 12×1 sensor arrays, it should be understood that other embodiments may include single recessed surface 82 or may include three or more recessed surfaces 82 for receiving sensor arrays. Further, while the recessed surfaces 82 are described as configured to receive 12×1 sensor arrays, it should be understood that embodiments are not limited to receiving 12×1 sensor arrays. Embodiments may have recessed surfaces to receive other sensor arrays configurations (e.g., 2×1 sensor arrays, 3×3 sensor arrays, 4×4 sensor arrays, 4×3 sensor arrays, 4×6 sensors arrays or the like). Examples of array geometries include, but are not limited to, rectangular, hexagonal, and arrays with staggered rows or columns.

Recessed surface 86 may be further recessed than recessed surface 82 so that the received pressure actuator may urge the received pressure sensors against the wrist of the user. In some embodiments, the recessed surface 86 may be configured to receive a fluid bladder pressure actuator. The fluid bladder actuator may be configured to be filled with various amounts of fluid to urge a received pressure sensor against a wrist with vary amounts of pressure. Some embodiments may include a fluid bladder pressure sensor for providing a signal indicative of the fluid pressure within the bladder. The recessed surface 86 and the received fluid bladder may extend transverse to the recessed surfaces 82 so that a single fluid bladder may be actuated to urge a plurality of received pressure sensor arrays against the wrist of the user with a single actuation. The bladder actuator in recessed surface 86 may also be configured as an array of bladders to actuate the pressure sensor or sensor array.

The device 74 may be configured to carry out the exemplary method 10. In some embodiments, the exemplary device 74 may be used to monitor blood pressure using applanation tonometry where a received pressure actuator in recess 86 is configured to perform a pressure sweep in the Z direction for identifying an MAP and then actuated to apply a preferred pressure so that the pressure sensor(s) provide continuous blood pressure monitoring.

Figure 8:
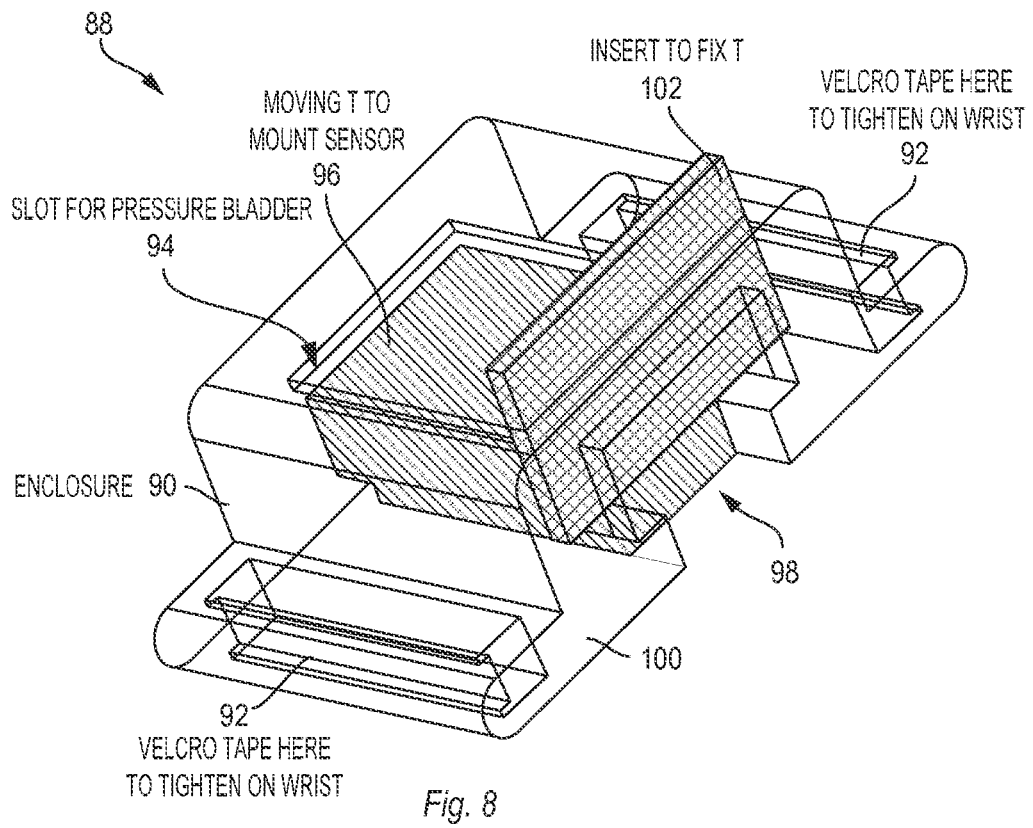
FIG. 8 illustrates yet another wrist-worn device for measuring pressure pulses at the wrist of the user according to embodiments of the present invention.

FIG. 8 illustrates another exemplary device 88 for monitoring and/or measuring blood pressure of a user. Exemplary device 88 may include an enclosure 90 having slots 92 for receiving a wrist strap for coupling the device 88 to a wrist of a user. Enclosure 90 may include a slot 94 for receiving a pressure bladder or other type of actuator. Enclosure 90 may further house a driver 96 and disposed between the received pressure actuator and pressure sensor. The device 88 may further include a pressure sensor (not shown) coupled to a surface of the driver 96 that is opposite a surface that couples with the received pressure actuator. The pressure sensor or pressure sensor array can be attached to the moving part 96, then be urged against artery.

Similar to the embodiment 74 illustrated in FIG. 7, device 88 may receive straps through slots 92 for coupling the device 88 with a wrist of the user. Further, the received straps may be used to tighten or to urge the device 88 and a pressure sensor of the device 88 against the wrist of the user. The enclosure 90 may position a driver 96 between a pressure actuator (e.g., a fluid bladder) and a pressure sensor. The driver 96 may be configured to evenly distribute forces from the pressure actuator across the pressure sensor. This may be preferred when device 88 couples with a plurality of pressure sensors and where the pressure actuator comprises a pressure bladder. In some embodiments, a pressure bladder surface may project and retract unevenly or otherwise have a bulge that applies different amounts of pressure depending on a contact location along the bladder surface. Thus, with a pressure sensor array, some pressure sensors may be applied to a wrist with a different pressure compared to other pressure sensors in the array. A rigid driver 96 disposed between a fluid bladder and one or more pressure sensors of device 88 may alleviate these issues by evenly distributing pressure from the fluid bladder across the pressure sensor array.

In the illustrated embodiment, the driver 96 may have a cross section that generally resembles a "T" however other configurations are possible. The enclosure 90 may include a T opening 98 in a sidewall 100 of the enclosure 90. The opening 98 may be dimensioned to receive driver 96 during assembly of enclosure 90. Once the driver 96 is inserted within the enclosure 90, an insert 102 may be positioned between the driver 96 and the opening 98 to secure the driver 96 within the enclosure 90.

Device 88 may couple with capacitive, piezoelectric film, piezoresistive pressure sensors or the like for measuring pressure. Further while discussed as using a fluid bladder as a pressure actuator, other actuators may be used (e.g., linear actuators, solenoids or the like). In some embodiments, utilizing one or more fluid bladders, fluid bladder pressure sensors may be used to provide a signal indicative of a fluid pressure with the one or more bladders.

Similar to the embodiments described above, the device 88 may be used to carry out method 10. Further in some embodiments, the exemplary device 88 may be used to monitor blood pressure using applanation tonometry where a received pressure actuator (e.g., fluid bladder) in slot 84 is configured to perform a pressure sweep in the Z direction by urging driver 96 and coupled pressure sensors against the wrist for identifying an MAP and then actuated to apply a preferred pressure so that the pressure sensor(s) provide continuous blood pressure monitoring.

Figure 9:
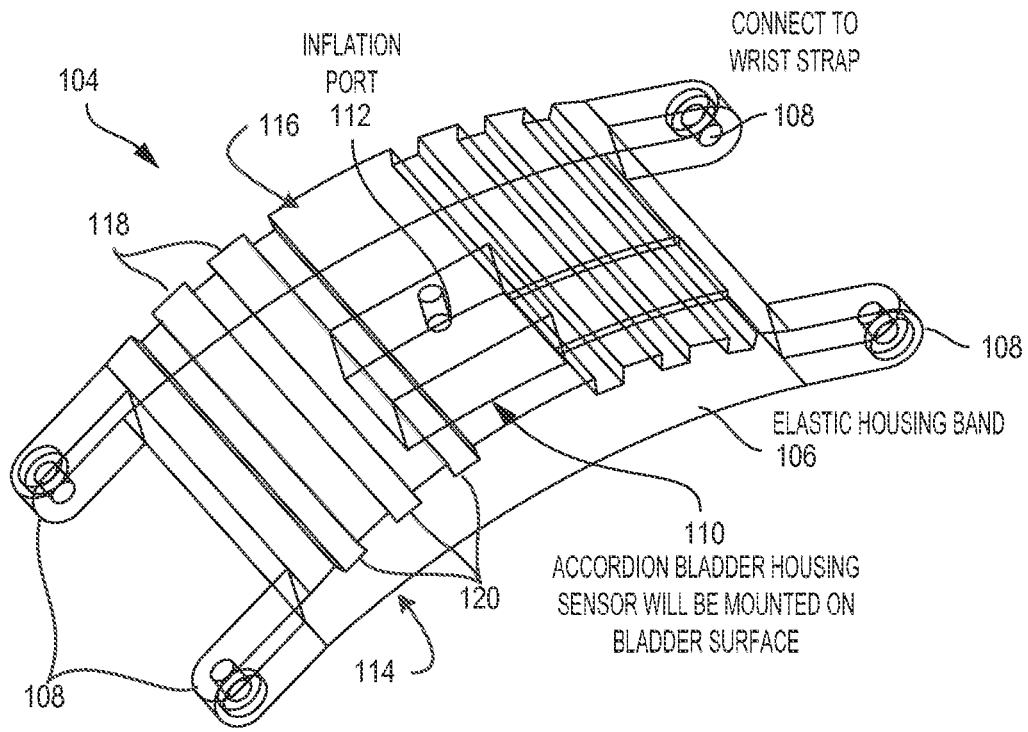
FIG. 9 illustrates yet another wrist-worn device for measuring pressure pulses at the wrist of the user according to embodiments of the present invention.

FIG. 9 illustrates yet another exemplary device 104 for measuring or monitoring blood pressure of a user. The exemplary device 104 includes an elastic housing band 106 configured to couple with a wrist of a user. The elastic housing band 106 may include engagement features 108 for coupling to a wrist strap. The elastic housing band 106 may further define a housing for receiving a fluid bladder 110. An inflation port 112 may extend from the fluid bladder housing 110 to an outer surface of the elastic housing band 106.

Elastic housing band 106 may generally have a curved configuration with an inner surface 114 configured to match the curvature of a user's wrist. The outer surface of the elastic housing band 106 may include ribs 118 and grooves 120 that run transverse to a length of the elastic housing band 106. The ribs 118 and grooves 120 may be configured to provide additional flexibility in elastic housing band 106, thereby allowing elastic housing band 106 to better conform to the curvature of a user's wrists.

Fluid bladder housing 110 may be configured to receive a fluid bladder. In many embodiments the device 104 may include an accordion bladder for urging one or more pressure sensors against the wrist of the user. An accordion bladder may avoid applying varying pressure along a contact face of the bladder and may thereby provide even distribution of pressure along a pressure sensor or pressure sensor array.

Figure 10:
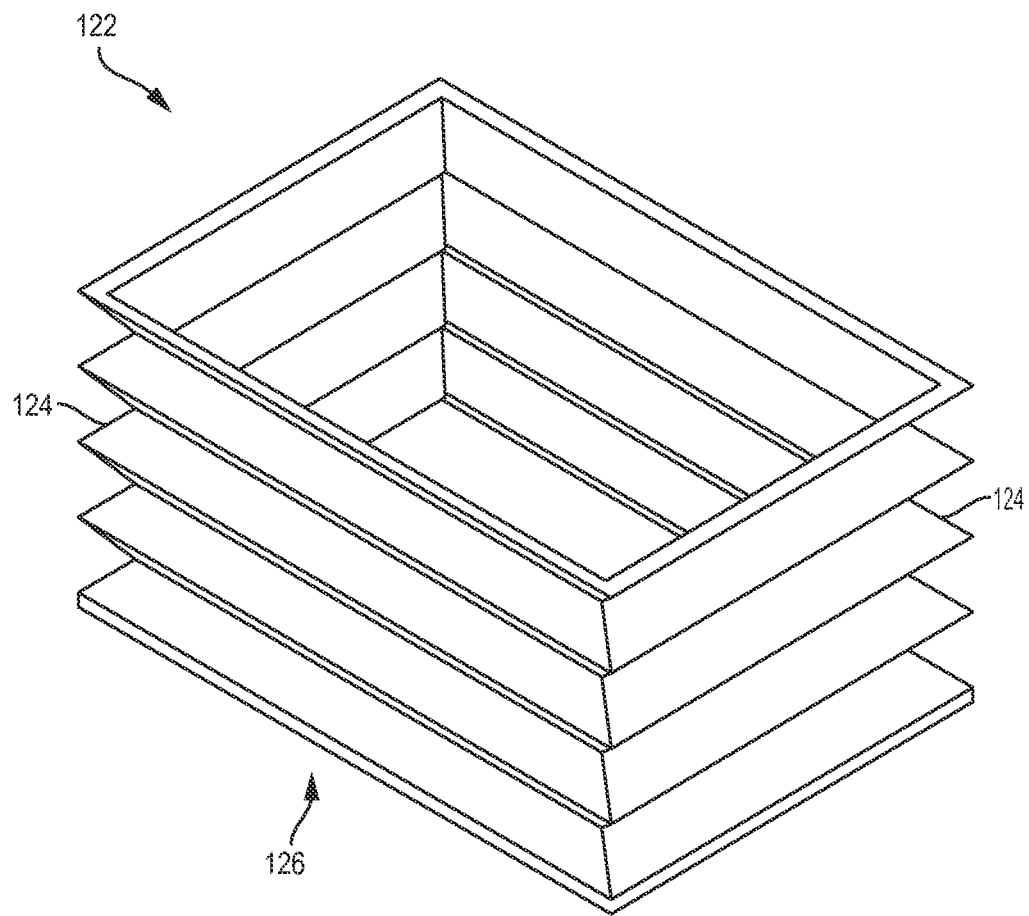
FIG. 10 illustrates a fluid bladder according to some embodiments of the present invention according to embodiments of the present invention.
Figure 11:
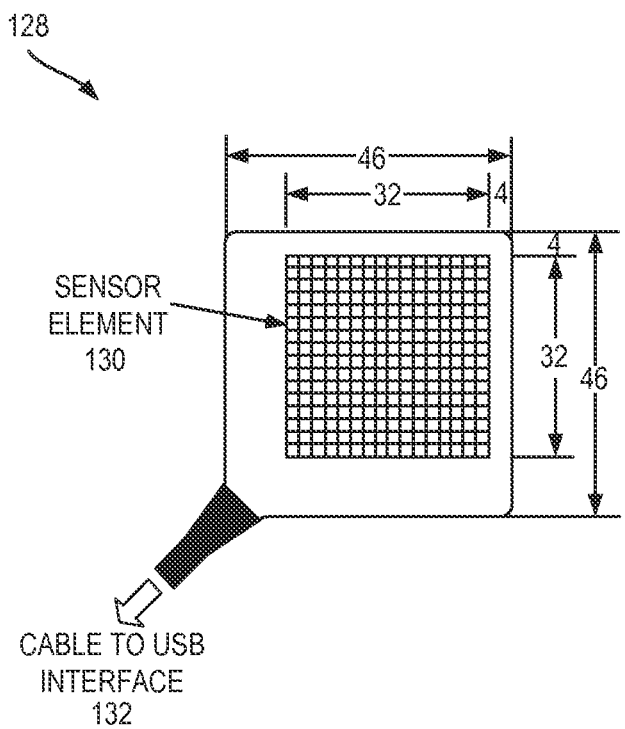
FIG. 11 illustrates a pressure sensor array that may be used with embodiments described herein according to embodiments of the present invention.

FIG. 10 illustrates an exemplary accordion bladder 122. Accordion bladder 122 may have side walls 124 that generally define a volume for receiving fluid for expanding accordion bladder 122 a desired amount. The defined volume may be in fluid communication with inflation port 122. The side walls 124 may be generally defined by a plurality of pleats or bellows that expand and contract with the filling and removal of fluid from the bladder 122. Accordion bladder 122 may further include a generally flat distal face 126 for coupling with a pressure sensor or pressure sensor array. Due to the accordion configuration of the bladder 122, fluid filling of the bladder 122 projects the distal face 126 of the bladder 122 linearly and evenly, thus increasing surface contact between the bladder 122 and a pressure sensor or array of sensors and reducing a bladder intramural stress. In this case the fluid pressure inside the bladder will be evenly exerted on surface 126 and been acting directly on the sensor or sensor array, and in turn to the artery. Pressure may then be applied to the pressure sensor/pressure sensor array and the wrist evenly. Accordingly, in some embodiments, a need for a driver disposed between the pressure actuator and the pressure sensor/pressure sensor array may be avoided by using such a bladder 122. The accordion type bladder can be made of thermoplastics (e.g. nylon, polyethylene, Teflon, etc.).

Device 104 may couple with capacitive, piezoelectric film, piezoresistive MEMS pressure sensors or the like for measuring pressure. Further while discussed as using a fluid bladder as a pressure actuator, other actuators may be used (e.g., linear actuators, solenoids or the like). In some embodiments, utilizing one or more fluid bladders, fluid bladder pressure sensors may be used to provide a signal indicative of a fluid pressure with the one or more bladders and the signal may be used for calibrating one or more pressure sensors of the device.

Similar to the embodiments described above, the device 104 may be used to carry out method 10. Further in some embodiments, the exemplary device 104 may be used to monitor blood pressure using applanation tonometry where a received pressure actuator (e.g., accordion fluid bladder) in fluid bladder housing 110 is configured to perform a pressure sweep in the Z direction by urging a coupled pressure sensor/pressure sensor array against the wrist for identifying an MAP and then actuated to apply a preferred pressure so that the pressure sensor(s) provide continuous blood pressure monitoring.

Figure 1:
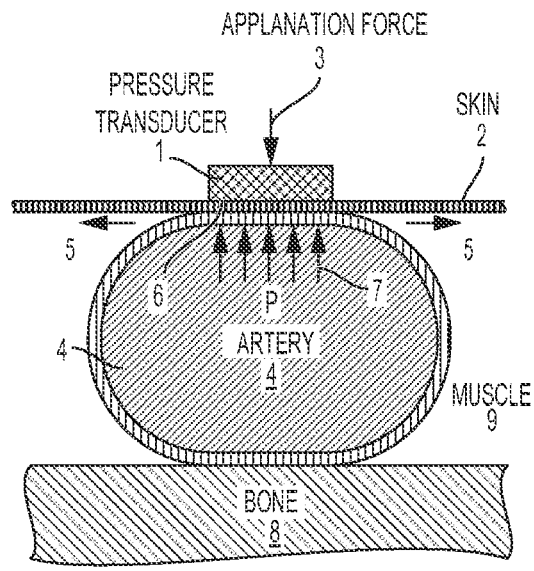
FIG. 1 shows a prior art method of applanation tonometry.
Figure 2:
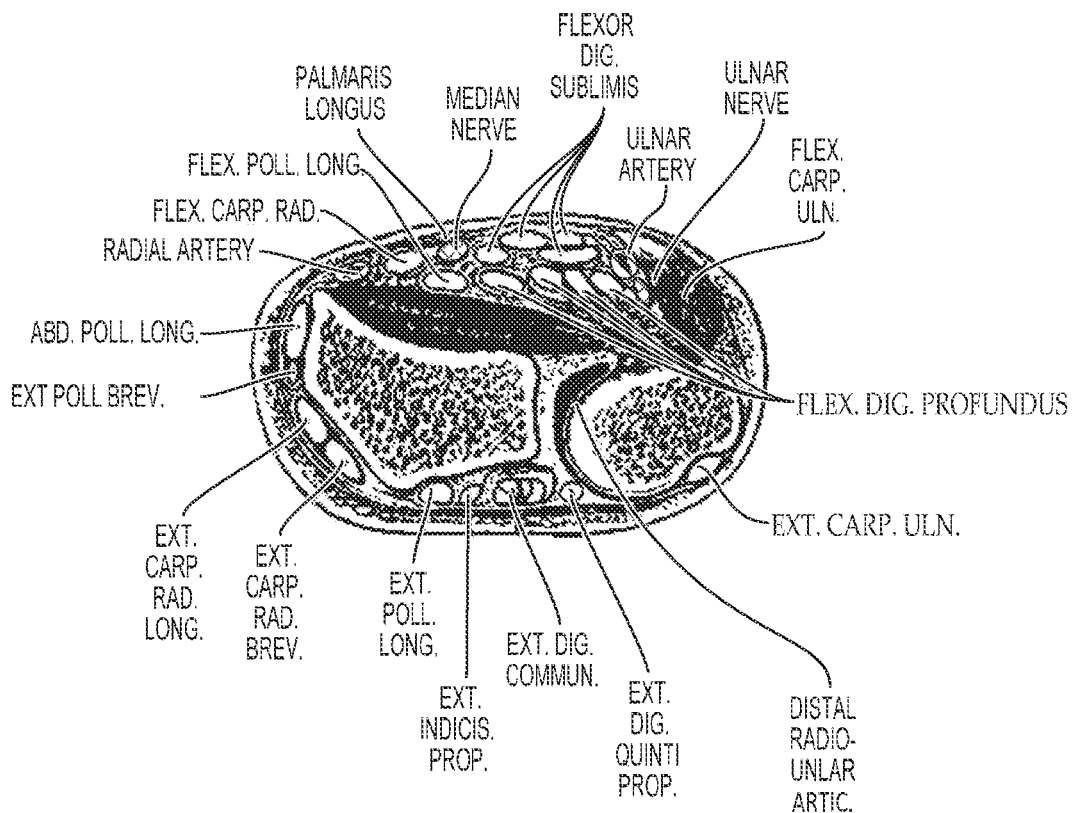
FIG. 2 shows the cross section of a wrist.

FIG. 1 shows an exemplary pressure sensor array 128 that may be used with the devices and methods described above. Pressure sensor array 128 may be 46 mm×46 mm in dimension and may comprises a plurality of capacitive pressure sensors 130 arranged in a 16×16 array. The pressure sensor array 128 may include a cable 132 to couple the pressure sensor array to a processing device (controller).

Each element may be approximately 2 mm×2 mm in size, thus providing an active area size of 32 mm×32 mm. The thickness of the active area may be approximately 1 mm. A scan rate may be up to 39 Hz.

Figure 12:
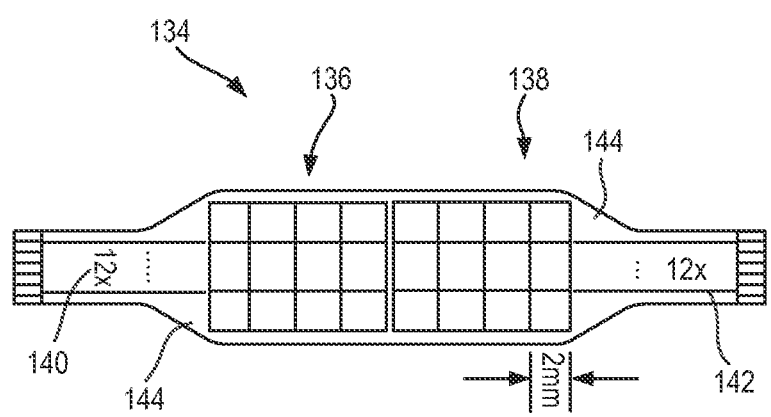
FIG. 12 illustrates another pressure sensor array that may be used with embodiments described herein according to embodiments of the present invention.

FIG. 12 illustrates another exemplary pressure sensor array 134. The array 134 comprises a first array 136 and a second array 138. The first array 136 may comprise a 4×3 capacitive pressure sensor array and the second array 138 may similarly comprise a 4×3 capacitive pressure sensor array. Each pressure sensor may be 2×2 mm. Accordingly the array 134 may have an active area size of 16 mm×6 mm. The wiring 140 associated with the first array 136 may be routed to a first side of the pressure sensor array 134 and the wiring 142 associated with the second array 138 may be routed to a second side of the pressure sensor array 134. Wiring 140, 142 may each comprise twelve wires that correspond to each of the pressure sensors in the respective arrays.

The first array 136 and the second array 138 may be symmetric so that the application of this sensor array 134 against the user's wrist may also symmetric. This type of array 134 may reduce the cantilever beam loading situation (when sensor array with only one side wiring structure is been pressed against artery, the array will undergo a bending mode between sensor array and wiring pack) and provide a more symmetric load on the sensor array 134.

The wiring 140, 142 for the sensor array 134 may be backed by a fabric material 144 (e.g., a cloth material). A fabric backing material 144 may facilitate installation within a monitoring device and may also reduce undesired bending or stretching loads being applied to the sensor array 134.

Figure 13:
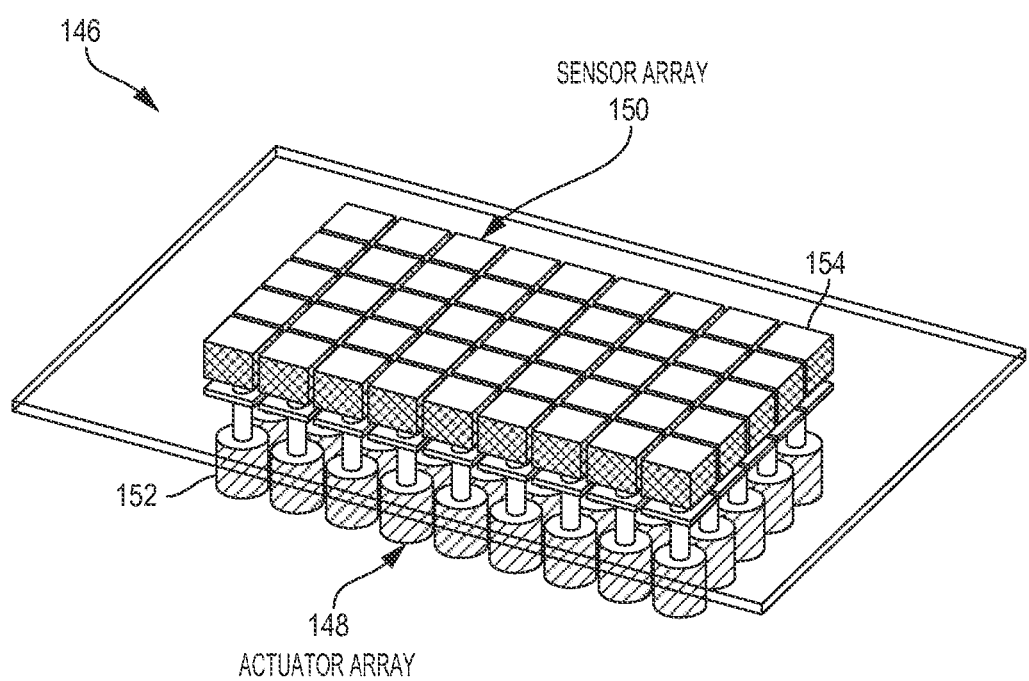
FIG. 13 illustrates a sensor array supported by an actuator array that may be used with embodiments described herein according to embodiments of the present invention.

FIG. 13 illustrates an exemplary pressure actuator-pressure sensor assembly 146 that may be used with the devices and methods disclosed herein. Assembly 146 may include an actuator array 148 coupled with a sensor array 150. Each actuator 152 of the actuator array 148 may be coupled to a pressure sensor 154 in the pressure sensor array 150. Each of the actuators 152 in the pressure actuator array 148 may be individually controlled to urge each of the pressure sensors 154 of the pressure sensor array 150 against a wrist/target artery of the user by different amounts. For example, different sensors may be urged different distances or amounts depending on the curvature, contours, or location on the wrist where the sensor is to be urged against. Thus some embodiments, may be configured to tailor to different user wrist curves and contours and may thereby provide more accurate pressure measurements. Accordingly, subsets of the pressure sensor array may be urged against different portions of the wrist. Based on pressure sensor readings, a preferred sensor, sensor location, or sensor signal may be identified and used for blood pressure measurements and/or monitoring.

In some instances when a constant actuation pressure (e.g., 80 mmHg) is applied, the sensor array element with the largest static pressure value may be different from the element with the largest dynamic pressure value. In such instances, the actuator can be moved or a different actuator can be used at a different position until the same element exhibits the largest static pressure as well as the largest dynamic pressure when a constant actuation pressure is applied.

While the array of actuators 148 is illustrated as a 5×9 array and the array of sensors 150 similarly illustrated as a 5×9 array, other array sizes are possible (e.g., smaller or larger). Further, the actuators 152 are illustrated as linear actuators, however other actuators may be used, including but not limited to, fluid bladders, rails actuators, solenoids, or the like. The pressure sensors 154 may be capacitive, piezoresistive, piezoelectric film sensor or the like. The pressure sensor array can be mounted entirely with some backing material to the linear actuator array, or individual elements may be mounted on individual actuators to form the entire array.

Figure 14:
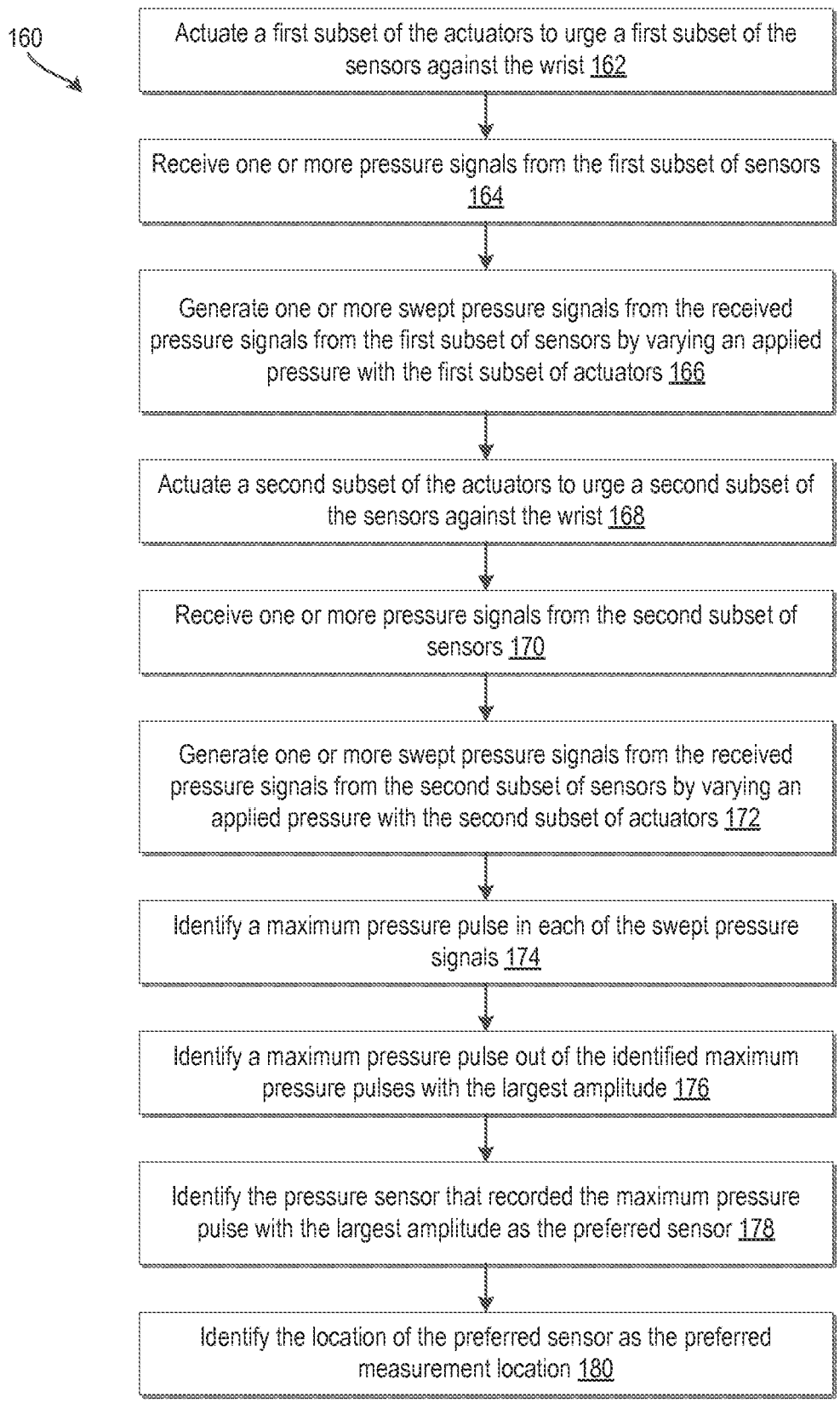
FIG. 14 illustrates a method of selectively actuating subsets of the plurality of pressure sensors against a wrist of a user according to embodiments of the present invention

FIG. 14 illustrates an exemplary method 160 of operating the exemplary assembly 146 of FIG. 13. At step 162, a first subset of the actuators are activated to urge a first subset of the sensors against the wrist. Pressure signals from the first subset of pressure sensors may then be received 164. One or more swept pressure signals may be received by varying an applied pressure with the first subset of actuators 166. Thereafter, a second subset of the actuators may be activated to urge a second subset of the sensors against the wrist 168. One or more pressure signals from the second subset of sensors may then be received 170. One or more swept pressure signals may be generated by varying the applied pressure with the second subset of actuators 172. A maximum pressure pulse may then be identified in each of the swept pressure signals 174. A maximum pressure pulse with the largest amplitude out of the identified maximum pressure pulses may then be identified 176. In some embodiments, the method may include identifying the pressure sensor that recorded the maximum pressure pulse with the largest amplitude 178 and identifying a location of the identified sensor relative to the wrist of the user 180. In some embodiments, the identified sensor and the identified location may be a preferred sensor and location that most closely identifies a blood pressure of the user and may be used for MAP measurements and blood pressure monitoring via applanation tonometry.

The first/second subset of actuators and the first/second subset of pressure sensors may be a single actuator and a single pressure sensor or may be more than one actuator and more than one sensor. In some embodiments, the first subset of actuators and sensors may be a first half of an array of actuator-sensor assemblies, while the second subset of actuators and sensors may be a second half of the array of actuator-sensor assemblies. In some embodiments, the first subset may be a quarter of an array of actuator-sensor assemblies, and the second subset may be another quarter of the array of actuator-sensor assemblies. Where the first subset and the second subset of actuator-sensor assemblies are less than the total number of actuator-sensor assemblies of the device, the method 160 may be repeated for additional subsets of actuator-sensor assemblies that remain.

While discussed as generating the swept pressure signal by varying the pressure applied by a coupled actuator, a swept pressure signal may, in some embodiments be generated by a change in height of the wrist relative to the heart of the user similar to embodiments described above. However, in many embodiments, a passive method (i.e., that does not require user arm movement) may be preferable as such methods may be performed with little to no inconvenience to the user.

Further, in some embodiments, prior to receiving the one or more pressure signals from the second subset of sensors 170, the first subset of sensors may be retracted away from the wrist.

Additionally, while method 160 is described with steps for processing the data by identifying a maximum pressure pulse with the largest amplitude out of a plurality of identified maximum pressure pulses within each pressure signal, other methods of signal analysis may be provided.

Figure 15:
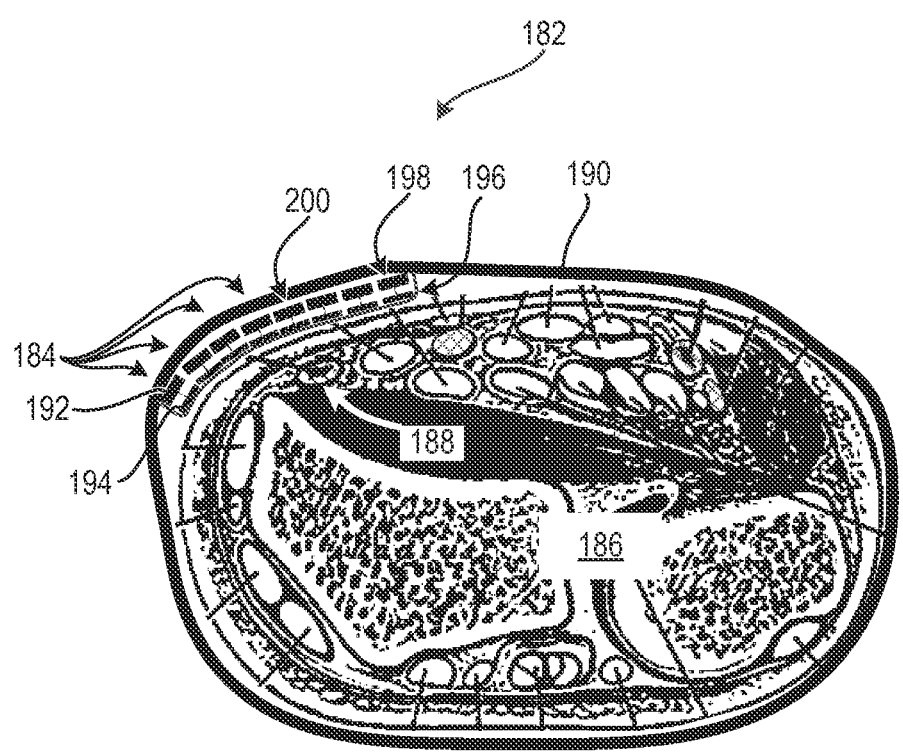
FIG. 15 illustrates the coupling of a device having a plurality of sensors and a plurality of actuators to a wrist of a user according to embodiments of the present invention.

FIG. 15 illustrates the coupling of a device 182 having a plurality of sensor-actuator assemblies 184 to a wrist 186 of a user according to embodiments of the present invention. The device 182 may be configured to measure the blood pressure of a user through applanation of the radial artery 188.

The device 182 includes a strap 190 extends around the wrist 186 and supports each of the plurality sensor-actuator assemblies 184 against the wrist 186. The sensor-actuator assemblies 184 may comprise an actuator 192 coupled with a pressure sensor 194. The plurality of sensor-actuator assemblies 184 may couple with the wrist 186 at a device skin interface 196.

The actuators 192 may be configured to selectively and/or sequentially urge regions of the skin interface 196 adjacent the respective actuators 192 and disposed between the actuators 192 and the wrist against the wrist 186 of the user. The coupled pressure sensor 194 may measure pressure experienced between the actuators 192 and the wrist 186 and provide a respective pressure signal to a processor (not shown). Accordingly, the skin interface 196 may comprise a plurality of regions along the wrist 186. While illustrated as a cross-section, it should be understood that skin interface 196 may comprise an array of regions that correspond to an array of actuators 192.

As illustrated, the skin interface 196 of the device 182 is generally disposed over the radial artery 188. While the radial artery 188 has a small footprint, a sensor or sensor array that covers a large region of the wrist circumference may ensure that the sensor or at least one sensor of a sensor array is positioned and/or oriented over the radial artery 188 in a desired manner. In some embodiments, given that not all sensors 194 of the device 182 are in a preferred position (e.g., where the face of the sensor is perpendicular to a pressure pulse from the target artery), it may be preferable to identify a preferred sensor 194 and a preferred region for applanation of the radial artery 188. This may be carried out by analyzing and comparing the signals from the plurality of sensors 194. For example, the sensors 194 disposed further from the radial artery 188 may provide weaker pressure signals that are not as meaningful for determining a blood pressure of a user.

In the illustrated embodiment with a plurality of sensors 194, the actuators 192 may be selectively and/or sequentially activated to urge different regions of the skin interface 196 against the wrist 186 in order to identify a preferred region for applanation of the radial artery 188. The preferred region for applanation of the radial artery 188 may be identified based on pressure signals received from the one or more sensors 194 of the device 182. For example, the skin interface region disposed between sensor-actuator assembly 198 may be urged against the wrist 186 and a signal may be received from the corresponding sensor 194 of sensor-actuator assembly 198. Additionally, the skin interface region disposed between the sensor-actuator assembly 200 may be urged against the wrist 186 and a signal may be received from the corresponding sensor 194 of the sensor-actuator assembly 200. The signals from the sensor of assembly 198 and the sensor of assembly 200 may then be compared to determine which signal is stronger and/or preferred. Given that the sensor-actuator assembly 200 is positioned closer to radial artery 188 and that the surface face of the sensor of assembly 200 is more perpendicular to pressure pulses from the radial artery 188, the signal from the sensor of assembly 200 may be stronger and preferred in comparison to the signal of the sensor of assembly 198 as it is further from the radial artery 188 and oriented at an angle relative to pressure pulses from the artery 188 and may suffer from increased signal loss.

The regions of the skin interface 196 may be selectively urged such that subsets of the regions of the skin interface 196 are urged against the wrist 186 at a time. The subsets of regions may be urged by multiple actuators 192 where a subset of the actuators 192 are activated (e.g., half the actuators, a quarter of the actuators, a single actuator etc.). Accordingly, in some embodiments the subsets of regions may each be urged selectively and sequentially by a single actuator 192 for identifying a preferred region and sensor 194.

FIG. 16 illustrates the selective actuation of a single region of a skin interface 210 against a wrist of a user according to embodiments of the present invention. Device 201 may include pressure sensors 202 that may be coupled with one of a plurality of actuators 204. The actuators 204 may be supported adjacent the wrist by a strap 206. The sensors 202 may couple with the skin 208 of the user via skin interface 210. As illustrated in FIG. 16, in some embodiments, a single region of the skin interface 210 disposed between an actuator 204 and the wrist may be urged against the wrist for applanation of the artery 212 using a single actuator 204. While applanating the artery 212 with the single actuator 204, the remaining actuators 204 may not be actively urging respective regions of the skin interface 210 against the wrist. This manner of actuation of regions of the skin interface 210 against the wrist may be performed selectively and sequentially in order to identify a preferred region for applanation of the artery 212 and a preferred sensor signal from one of the sensors 202.

FIG. 17 illustrates device 201 selectively actuating more than one region of a skin interface 210 against a wrist of the user according to embodiments of the present invention. As illustrated in FIG. 17, a subset of regions (e.g., the right half the regions) of the skin interface 210 positioned between actuators 204 and the wrist are urged against a wrist of a user by activating two of the actuators 204 while the other two actuators 204 may not be actively urging respective regions of the skin interface 210 against the wrist. In some embodiments, pressure signals may only be processed from the advanced pressure sensors 202. In some embodiments, pressure signals may only be received from the advanced pressure sensors 202. In some embodiments, the received pressure signals may be processed to identify a blood pressure of the user or compared to identify a preferred pressure sensor 202 between the two advanced pressure sensors 202 and a preferred region for applanation. In such a method, processing time may be reduced as only a subset of pressure signals may be received from the subset urged regions.

While FIG. 15-FIG. 17 illustrate devices with a plurality of individual sensors 202, other embodiments may utilize a sensor system comprising a pressure film sensor. For example, FIG. 18 illustrates a device 300 that includes a pressure film sensor 302 that may be coupled with a plurality of actuators 304. The actuators 304 may be supported adjacent the wrist by a strap 306. The sensor 302 may couple with the skin 308 of the user via skin interface 310. As illustrated in FIG. 18, in some embodiments, a single region of pressure film sensor 302 and a single region of the skin interface 310 may be urged against the wrist for applanation of the artery 312 using a single actuator 304. While applanating the artery 312 with the single actuator 304, the remaining actuators 304 may not be actively urging respective regions of the pressure film sensor 302 and the skin interface 310 against the wrist. This selective actuation of regions of the pressure film sensor 302 against the wrist may be performed selectively and sequentially in order to identify a preferred region of the pressure film sensor 302 and skin interface 310 for applanation of the artery 312.

FIG. 19 illustrates device 300 selectively actuating a subset of regions of a skin interface 310 and pressure film sensor 302 against a wrist of the user according to embodiments of the present invention. As illustrated in FIG. 19, a subset of regions (e.g., the right half the regions) of the skin interface 310 are urged against a wrist of a user by activating two of the actuators 304 on the right while the other two actuators 304 on the left may not be actively urging the respective regions of the pressure film sensor 302 against the wrist. Regions of the pressure film sensor 302 may be selectively and/or sequentially urged against the wrist to identify a preferred region of the skin interface 310 for applanation of the target artery 312 and a preferred region of the pressure film sensor 302 for receiving pressure signals.

Figure 20A:
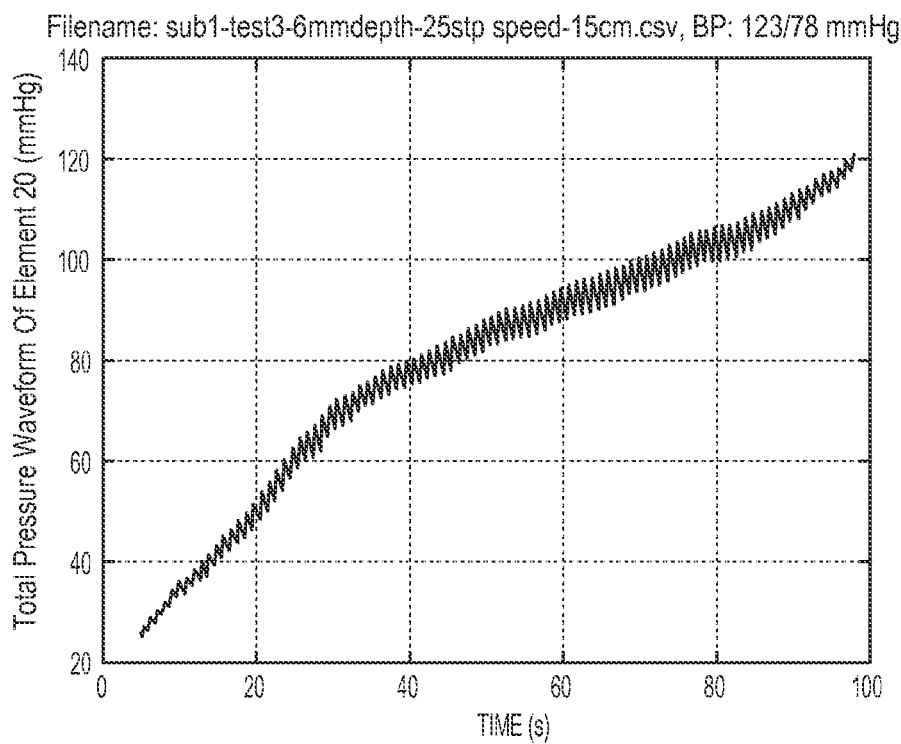
FIGS. 20A-20C show pressure sensor data obtained from an array of pressure sensors applied to a user according to embodiments of the present invention.
Figure 20B:
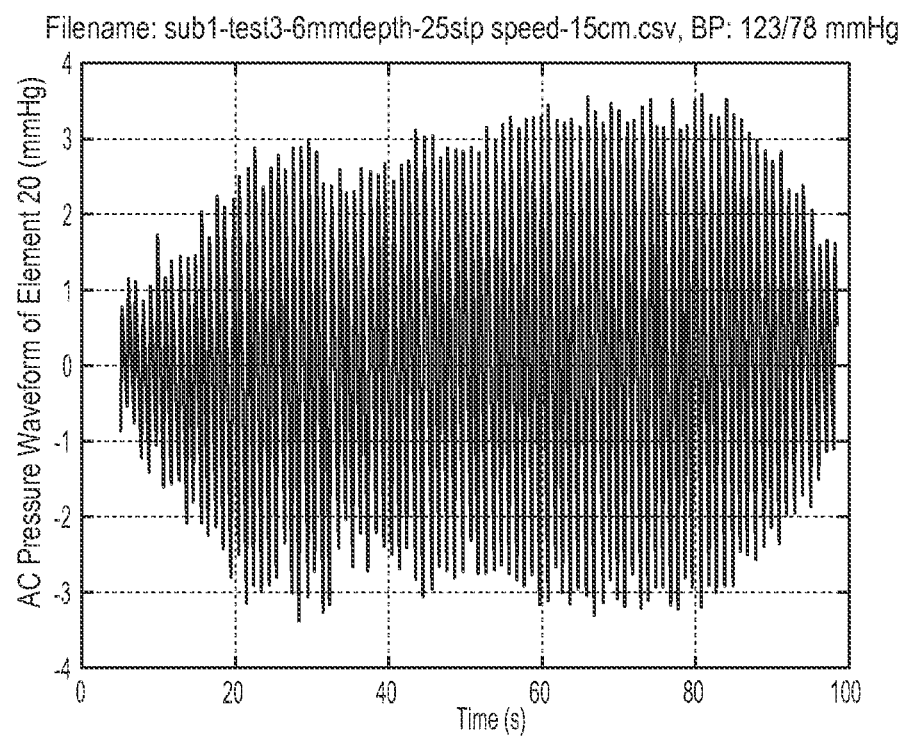
Figure 20C:
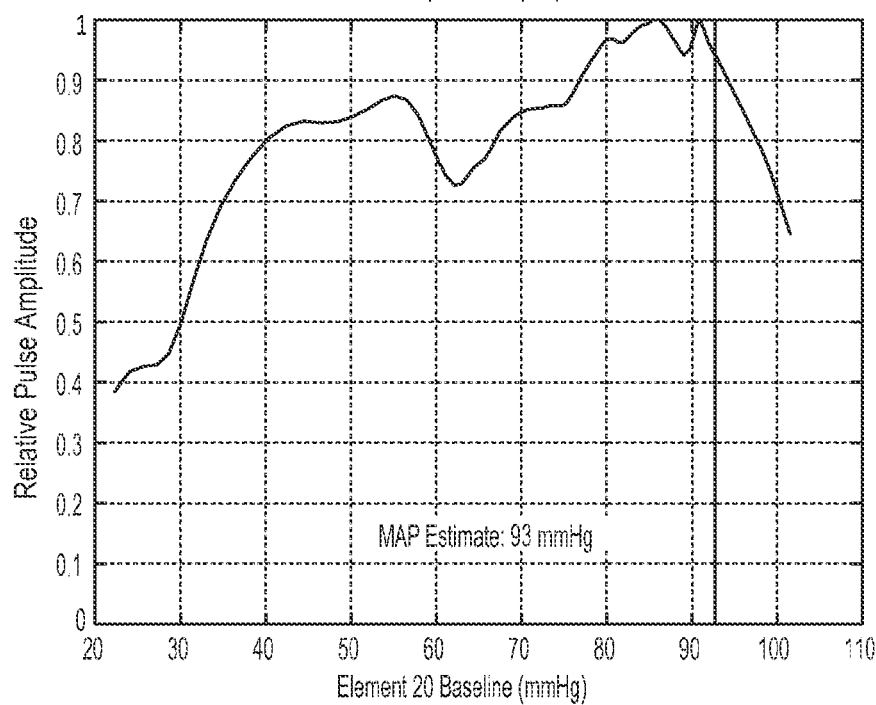

FIGS. 20A-20C show sensor data obtained from an array of pressure sensors applied to a user according to embodiments of the present invention. The data was received from a 1×12 array of pressure sensors applied to a subject's wrist at the radial artery. The pressure actuator was a linear actuator that traveled approximately 6 mm perpendicularly to the wrist surface with a speed of 25 steps/s (each step was approximately 38 μm (The wrist was approximately 15 cm below the heart. The reference blood pressure taken from an oscillometric brachial monitor was systolic blood pressure (123 mmHg) and diastolic blood pressure (78 mmHg). The reference mean arterial pressure was estimated by mean arterial pressure=⅓*(systolic blood pressure)+⅔*(diastolic blood pressure). The total (i.e., AC and baseline) pressure waveform from the sensor element with the strongest pulsatile (i.e., AC) component is illustrated in the pressure vs. time chart shown in FIG. 20A. The AC pressure waveform versus time for the same sensor element is illustrated in FIG. 20B. FIG. 20C shows the relative AC amplitude vs. baseline from the same sensor element. Element 20 had the largest pressure amplitude measurements while the remaining received relatively weaker pressure signals Accordingly, element 20 may be a preferred sensor and may be considered to be placed at a preferred region and/or orientation adjacent the target artery. Thus, in some embodiments, a blood pressure measurement may be calculated based on this pressure signal alone.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of measuring a blood pressure of a user having a wrist, skin defining an outer surface of the wrist, the method comprising:

maintaining engagement between the skin of the wrist and a skin interface of a wrist-worn device using a band having a length extending about the wrist, the wrist-worn device comprising actuators and a sensor system, the skin interface including an array of surface regions distributed along the length of the band, the sensor system comprising sensors, each of the sensors being associated with one of the surface regions, wherein each of the actuators is operatively coupled with only one of the sensors;

selectively urging a first region of the array at a first location of the band against the wrist with a first actuator and receiving a first associated signal from a first sensor of the sensors, the first sensor being associated with the first region;

selectively urging a second region of the array at a second location of the band against the wrist with a second actuator and receiving a second associated signal from a second sensor of the sensors, the second sensor being associated with the second region, wherein the first location is spaced apart from the second location along the length of the band;

selecting one of the first sensor and the second sensor by comparing the first associated signal with the second associated signal;

identifying a preferred actuator of the first actuator and the second actuator, wherein the preferred actuator is identified to be the first actuator when the selected one of the first sensor and the second sensor is the first sensor, and wherein the preferred actuator is identified to be the second actuator when the selected one of the first sensor and the second sensor is the second sensor;

measuring the blood pressure of the user via applanation by using the preferred actuator and the selected one of the first sensor and the second sensor; and outputting the blood pressure.

2. The method of claim 1, wherein selectively urging the first region of the array against the wrist of the user is performed concurrently with receiving the first associated signal so that the first associated signal is a first swept pressure signal comprising pressure waveforms measured while an applied pressure by the first actuator is varied; and wherein selectively urging the second region against the wrist of the user is performed concurrently with receiving the second associated signal so that the second associated signal is a second swept pressure signal comprising pressure waveforms measured while an applied pressure of the second actuator is varied.

3. The method of claim 2, wherein comparing the first associated signal with the second associated signal comprises identifying a first maximum pressure pulse in the first swept pressure signal and a second maximum pressure pulse in the second swept pressure signal and wherein the selected one of the first sensor and the second sensor is associated with the signal with a larger maximum pressure pulse amplitude.

4. The method of claim 1, further comprising withdrawing the first region from the wrist of the user prior to receiving the second signal from the sensor system.

5. The method of claim 1, wherein:
the first sensor comprises a first pressure sensor;
the second sensor comprises a second pressure sensor; and
selectively urging the first region of the array and selectively urging the second region of the array against the wrist is performed by urging the first pressure sensor against the wrist with the first actuator and by urging the second pressure sensor against the wrist with the second actuator, respectively.

6. A device for determining a blood pressure of a user having a wrist, skin defining an outer surface of the wrist and an artery; the device comprising:
an elongate band with a length configured to extend around the wrist of the user so as to support a skin interface surface of the device in engagement with the skin of the wrist;
pressure actuators coupling the elongate band to the skin interface surface, the pressure actuators configured to apply a variable pressure between the skin interface surface and the skin of the wrist at an array of regions distributed along the skin interface surface, the pressure actuators comprising a first pressure actuator and a second pressure actuator;
pressure sensors distributed over a sensor surface extending along the skin interface surface, the pressure sensors comprising a first pressure sensor and a second pressure sensor, the first pressure sensor being configured to sense a pressure of a first region of the array of regions, the second pressure sensor being configured to sense a pressure of a second region of the array of regions, wherein each of the pressure sensors is operatively coupled with only one of the pressure actuators;
a signal processing system coupled with the pressure sensors and the pressure actuators such that, in use, the first pressure actuator and the second pressure actuator selectively and sequentially urge the first region and the second region, respectively, against the wrist; wherein the first pressure sensor generates a first pressure signal while the first region is urged against the wrist by the first pressure actuator and the second pressure sensor generates a second pressure signal while the second region is urged against the wrist by the second pressure actuator, the first region being disposed at a first location of the band, the second region being disposed at a second location of the band, the first location being spaced apart from the second location along the length of the band, the signal processing system being configured to:
select one of the first pressure sensor and the second pressure sensor by comparing the first pressure signal with the second pressure signal;
identify a preferred pressure actuator of the first pressure actuator and the second pressure actuator, wherein the preferred pressure actuator is identified to be the first pressure actuator when the selected one of the first pressure sensor and the second pressure sensor is the first sensor, and wherein the preferred pressure actuator is identified to be the second pressure actuator when the selected one of the first pressure sensor and the second pressure sensor is the second pressure sensor; and
measure the blood pressure of the user via applanation by using the preferred pressure actuator and the selected one of the first pressure sensor and the second pressure sensor; and
output the measured blood pressure.

7. The device of claim 6, wherein the first pressure actuator and the second pressure actuator are each actuated individually so as to urge only one of the first region and the second region against the wrist at a time.

8. The device of claim 6, wherein at least one of the first pressure actuator and the second pressure actuator comprises a linear solenoid piston.

9. The device of claim 6, wherein at least one of:
the first pressure actuator comprises a first fluid bladder configured to be selectively filled with a fluid to drive the first pressure sensor a desired amount against the wrist and to be selectively deflated to reduce an amount of pressure applied by the first pressure sensor against the wrist; and
the second pressure actuator comprises a second fluid bladder configured to be selectively filled with a fluid to drive the second pressure sensor a desired amount against the wrist and to be selectively deflated to reduce an amount of pressure applied by the second pressure sensor against the wrist.

10. The device of claim 9, wherein at least one of the first fluid bladder or the second fluid bladder is selectively filled by a phase change of a filling fluid from a liquid to a gas.

11. The device of claim 9, further comprising a bladder pressure sensor configured to identify a pressure within at least one of the first fluid bladder or the second fluid bladder.

12. The device of claim 11, wherein at least one of the pressure sensors comprises a piezoelectric film pressure sensor.

13. The device of claim 12, wherein the blood pressure of the user is calculated from piezoelectric film pressure measurements by calibrating the piezoelectric film pressure measurements with the pressure identified within the at least one of the first fluid bladder or the second fluid bladder.

14. The device of claim 6, wherein at least one of the pressure sensors comprises a piezoresistive pressure sensor.

15. The device of claim 6, wherein the pressure sensors are arranged in an array having a first dimension of at least 12 and a second dimension of at least 1.

16. The device of claim 6, wherein the pressure sensors are arranged in an array having a first dimension of at least 3 and a second dimension of at least 4.

17. The device of claim 6, wherein the device is configured to calculate the blood pressure of the user without user interaction or periodic calibration.

* * * * *